US010064551B2

(12) United States Patent
Cosentino et al.

(10) Patent No.: US 10,064,551 B2
(45) Date of Patent: Sep. 4, 2018

(54) HEALTH-MONITORING SYSTEM WITH MULTIPLE HEALTH MONITORING DEVICES, INTERACTIVE VOICE RECOGNITION, AND MOBILE INTERFACES FOR DATA COLLECTION AND TRANSMISSION

(71) Applicant: Cardiocom, LLC, Chanhassen, MN (US)

(72) Inventors: Daniel L. Cosentino, Excelsior, MN (US); Brian A. Golden, Eden Prairie, MN (US); Kristin N. Parrott, Jordan, MN (US); Christopher T. Abrahamson, Bloomington, MN (US)

(73) Assignee: Cardiocom, LLC, Minneapolis, MN (US)

( * ) Notice: Subject to any disclaimer, the term of this patent is extended or adjusted under 35 U.S.C. 154(b) by 1282 days.

(21) Appl. No.: 13/856,824

(22) Filed: Apr. 4, 2013

(65) Prior Publication Data
US 2013/0267795 A1    Oct. 10, 2013

Related U.S. Application Data

(60) Provisional application No. 61/620,371, filed on Apr. 4, 2012.

(51) Int. Cl.
*A61B 5/00* (2006.01)
*G06F 19/00* (2018.01)

(52) U.S. Cl.
CPC .......... *A61B 5/0002* (2013.01); *A61B 5/0022* (2013.01); *A61B 5/742* (2013.01);
(Continued)

(58) Field of Classification Search
None
See application file for complete search history.

(56) References Cited

U.S. PATENT DOCUMENTS 5,967,975 A * 10/1999 Ridgeway ........... G06F 19/3418
600/300
6,416,471 B1 * 7/2002 Kumar ................. G06F 19/323
128/903

(Continued)

OTHER PUBLICATIONS

Invitation to Pay Additional Fees with Partial International Search for PCT/US2013/035271 dated Nov. 4, 2013.

*Primary Examiner* — Niketa Patel
*Assistant Examiner* — Qingjun Kong

(57) ABSTRACT

This disclosure describes a remote patient monitoring system configured to monitor one or more patient parameters via one or more monitoring apparatuses for transmitting patient data to a remote, central data-processing facility via a network. The system further includes an interactive voice recognition ("IVR") system and mobile interfaces for health data collection and transmission via direction communication with the patient. According to embodiments, with the information received from the patient monitoring system, one or more scored indicative of a patient's health status is calculated. The scores are compared to threshold values and, based on the comparisons, further action is taken. For example, a medical caregiver can evaluate the patient's condition, including the effectiveness of the drug therapy, patient compliance, whether the patient's condition is improving, whether the patient requires hospitalization or an office consultation to prevent the condition from getting worse, etc. Enabling medical caregivers to remotely monitor and manage a patient's condition may reduce hospitalizations by early identification of health issues.

17 Claims, 12 Drawing Sheets

(52) U.S. Cl.
CPC ............ *A61B 5/7405* (2013.01); *A61B 5/746* (2013.01); *A61B 5/7465* (2013.01); *G06F 19/3418* (2013.01); *A61B 2505/07* (2013.01); *A61B 2560/0295* (2013.01)

(56) References Cited

U.S. PATENT DOCUMENTS

| | | | | |
|---|---|---|---|---|
| 2002/0002325 | A1* | 1/2002 | Iliff | G06Q 50/22 600/300 |
| 2009/0216558 | A1* | 8/2009 | Reisman | G06F 19/328 705/3 |
| 2009/0234916 | A1* | 9/2009 | Cosentino | G06F 19/322 709/203 |
| 2013/0137937 | A1* | 5/2013 | Dziubinski | G06F 19/322 600/300 |
| 2014/0184422 | A1* | 7/2014 | Mensinger | A61B 5/0004 340/870.02 |

\* cited by examiner

HEALTH-MONITORING SYSTEM WITH MULTIPLE HEALTH MONITORING DEVICES, INTERACTIVE VOICE RECOGNITION, AND MOBILE INTERFACES FOR DATA COLLECTION AND TRANSMISSION

REFERENCE TO CO-PENDING APPLICATION

This application claims the benefit of priority of U.S. Provisional Application No. 61/620,371, filed Apr. 4, 2012, and entitled, "HEALTH-MONITORING SYSTEM WITH CELLULAR-ENABLED HEALTH MONITORING DEVICES, INTERACTIVE VOICE RECOGNITION, AND MOBILE INTERFACES FOR DATA COLLECTION AND TRANSMISSION" the disclosure of which is incorporated by reference herein in its entirety.

INTRODUCTION

Patients suffering from chronic diseases, such as congestive heart disease, diabetes, renal failure, etc., undergo drug therapy and lifestyle changes to manage their medical condition. For such patients, certain patient parameters are monitored by a medical caregiver: weakness, fatigue, weight gain, edema, dyspnea (difficulty breathing or shortness of breath), nocturnal cough, orthopnea (inability to lie flat in bed because of shortness of breath), paroxysmal nocturnal dyspnea (awakening short of breath relieved by sitting or standing), body weight (an indication of response to drug therapy), oxygen saturation levels, blood pressure, and heart rate. Moreover, patients suffering from chronic diseases benefit when they comply with daily medication, diet, and exercise regimens. However, many times such patients are ambulatory and wish to reside in their own homes rather than in a healthcare facility. In this case, monitoring of patient parameters and patient compliance with prescribed therapies becomes a challenge. Patients and medical caregivers would benefit from a monitoring system suitable for home use capable of monitoring several wellness parameters.

In general terms, this disclosure is directed to systems and methods for collecting, transmitting, and processing health-related data. Data may be collected via one or more remote monitoring apparatuses configured to monitor one or more patient parameters. The remote monitoring apparatuses are configured to automatically and independently communicate patient data to a remote processing system for processing. The data may be collected, scored, and compared to threshold values. Based on the processing, further actions may be taken.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims herein as well as the appended drawings.

It is to be understood that both the foregoing general description and the following detailed description are exemplary and explanatory and are intended to provide further explanation for the appended claims.

DETAILED DESCRIPTION

Although the methods and monitoring apparatus introduced above and discussed in detail below may be useful in a variety of healthcare environments, the present disclosure will discuss the implementation of these techniques for use in remotely monitoring an ambulatory patient. The technology described in the context of a home-healthcare environment could be adapted for use in other healthcare environments that would benefit from remote-monitoring of a patient condition.

The embodiments described herein are implemented as a medical system and method capable of monitoring wellness parameters and physiological data of ambulatory patients and transmitting such parameters and data to a first remote location for processing. A medical professional, at either the first or a second remote location, monitors the patient's condition by accessing the transmitted data and any other data produced at the first remote location via one or more patient monitoring apparatuses. Based on this data, the medical professional provides medical treatment and/or communicates with the patient as may be necessary. Example devices which disclose applicable methods and systems are shown in the co-pending patent application entitled, DOWNLOADABLE DATASETS FOR A PATIENT MONITORING SYSTEM, filed Feb. 12, 2009, by Daniel L. Cosentino, et al., commonly assigned with the present application, which is incorporated by reference herein in its entirety.

This disclosure further describes a system having one or more remote monitoring apparatuses configured to monitor one or more patient parameters. Each of the remote monitoring apparatuses are arranged and configured to automatically and independently communicate patient data to a central-processing facility via any method of data communication. For example, the monitoring apparatuses may include an integrated cellular transceiver enabling the monitoring apparatus to transmit patient data to a central data-processing facility. The information from the monitoring apparatuses is received at the central data-processing facility and scored based on various health factors. Based on the scoring, the central-processing facility determines a next step. For example, the central-processing facility may determine to take further patient measurements, prompt secondary patient questions, and/or notify a medical caregiver so that the patient's health may be remotely evaluated by the medical caregiver.

Figure 1:
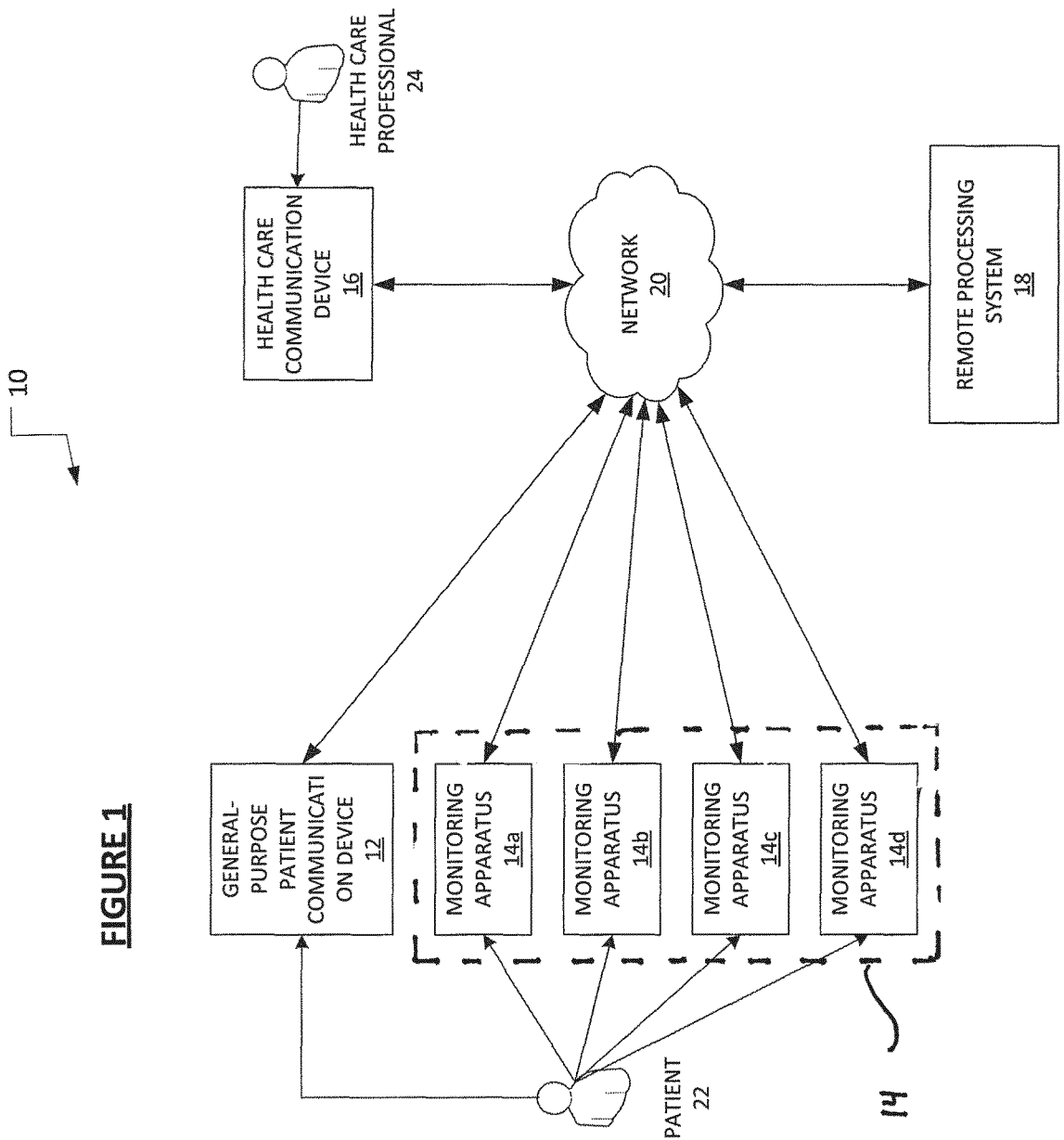
FIG. 1 is an illustration of an embodiment of a patient monitoring system.

FIG. 1 is an illustration of an embodiment of a suitable patient monitoring system 10. In general, the monitoring system 10 includes a general-purpose patient communication device 12, a plurality of suitable monitoring apparatuses 14a-f (collectively 14), a health care communication device 16, a remote processing system 18, and a network 20. A patient 22 interacts with the patient communication device 12 and the plurality of monitoring apparatuses 14. A health care professional 24 interacts with the health care communication device 16.

The general-purpose patient communication device 12 may be located in the home of an ambulatory patient, or in some other location that is easily accessible to the patient 22. In the embodiments shown, the device 12 is specifically a general-purpose device so that no purpose-built or dedicated device is needed by the patient in order to interact with the remote processing system 18. Examples of the general-purpose patient communication device 12 may include a telephone, a cellular telephone, a smart phone, a pager, a tablet computer, a personal computer, or other wireless or wired communication devices. The patient 22 may utilize the communication device 12 to communicate health-related data to the remote processing system 18.

The plurality of monitoring apparatuses 14 may also be located in the home of the ambulatory patient, or in some other location that is easily accessible to the patient 22. The monitoring apparatuses 14 may communicate to the remote processing system 18 via the network 20. Alternatively or additionally, the monitoring apparatuses 14 are configured to communicate via a cellular transceiver to the remote processing system 18. The monitoring apparatuses 14 are arranged and configured to monitor various wellness parameters of the patient 22 and then transmit these wellness parameters to the remote processing system 18.

The patient 22 can utilize the communication device 12 or any of the monitoring apparatuses 14 to transmit health-related data to the remote processing system 18 via the network 20. Alternatively, a family member of the patient 22 or other person in close proximity to the patient 22 and authorized by the patient 22 may utilize the communication device 12 or monitoring apparatuses 14 on behalf of the patient 22 to communicate data related to the patient 22 to the remote processing system 18.

The network 20 can be accessed to connect the patient 22 via the communication device 12, the monitoring apparatuses 14, and the health care professional 122. Examples of the network 20 include the Internet, public switched telephone network, or other network. The network 20 can be accessed by way of the general-purpose patient communication device 12, the monitoring apparatuses 14, the health care communication device 16, and any communication device that may be located at the remote processing system 18.

Health and wellness information about the patient 22 is transmitted to the remote processing system 18 through the communication device 12 and/or the monitoring apparatuses 14. The data from the multiple sources (e.g., communication device 12 and monitoring apparatuses 14) is received and processed at the remote processing system 18. For example, the data may be independently received and compiled by computing a score or multiple scores indicative of a health status of the patient 22. For example, scores may be calculated at the remote processing system 18 by assigning values to individual pieces of patient health data and comparing the values to predetermined threshold values indicating a suitable range for the values. Scores may also be continuously updated based on incoming information to the remote processing system 18. The threshold values may be predetermined and stored in the remote processing system 18, and may be individualized to the particular patient or generic to a group of patients. It is understood that in some embodiments, the steps of score calculation and/or score comparison to threshold values are conducted at the source of the data (e.g., communication device 12, monitoring apparatuses 14) prior to transmitting the data to the remote processing system 18. In such embodiments, the calculated scores and/or other score related data is also transmitted to the remote processing system 18.

Based on the calculated score or scores, the remote processing system 18 determines further actions. For example, the remote processing system 18 may determine to take additional patient measurements, prompt secondary health-related question hierarchies to the patient 22, and/or notify the health care professional 24. If the remote processing system 18 determines to take further patient measurements or prompt additional questions, the remote processing system 18 may utilize one or more of the communication device 12 and monitoring apparatuses 14 to accomplish such tasks. For example, the remote processing system 18 may remotely awaken one of the monitoring apparatuses 14 to alert the patient 22 to interact with the selected monitoring apparatus 14 to input further measurements or answer secondary questions. In some embodiments, the remote processing system 18 may determine a specified time or a time period when one or more of the monitoring apparatuses 14 will be triggered to automatically initiate a communication session with the patient 22. If the patient 22 does not transmit further data during the time period, for example, the processing system 18 may initiate further communication sessions with the patient 22 via the monitoring apparatuses 14 or the communication device 12, or simply alert the health care professional 24 of the patient's absence.

The remote processing system 18 is also arranged and configured to synchronize each of the monitoring apparatuses 14 and the communication device 12. For example, if a the monitoring apparatus 14a presents a first question or question hierarchy which is then answered by the patient 22, the remote processing system 18 ensures that the same questions are not presented to the patient 22 a second time by the monitoring apparatuses 14b-d or the communication device 12. Instead, based on the answers to the first question or question hierarchy, the remote processing system 18 may determine that a second question or question hierarchy must be presented to the patient 22. The remote processing system 18 may awaken any of the monitoring apparatuses 14, for example, to initiate a communication session with the patient 22 to present the additional question(s) to the patient 22. General information on the structure of question hierarchies is described in detail in the co-pending patent application entitled, DOWNLOADABLE DATASETS FOR A PATIENT MONITORING SYSTEM, filed Feb. 12, 2009, by Daniel L. Cosentino, et al., commonly assigned with the present application, incorporated by reference herein in its entirety above.

The health care communication device 16 may be located at a health care professional's office, health care oversight location, or any other location that is easily accessible to the health care professional 24. The health care professional 24 can access the patient information collected via the communication device 12 or the monitoring apparatuses 14. In some embodiments, the health care professional 24 may be located at the remote processing system 18 and therefore has direct access to the remote processing system 18. In other embodiments, such as that shown in FIG. 1, the health care professional 24 may be located at a different location than the remote processing system 18 and thus may access the remote processing system 18 through the health care communication device 16 by way of the network 20.

Figure 2:
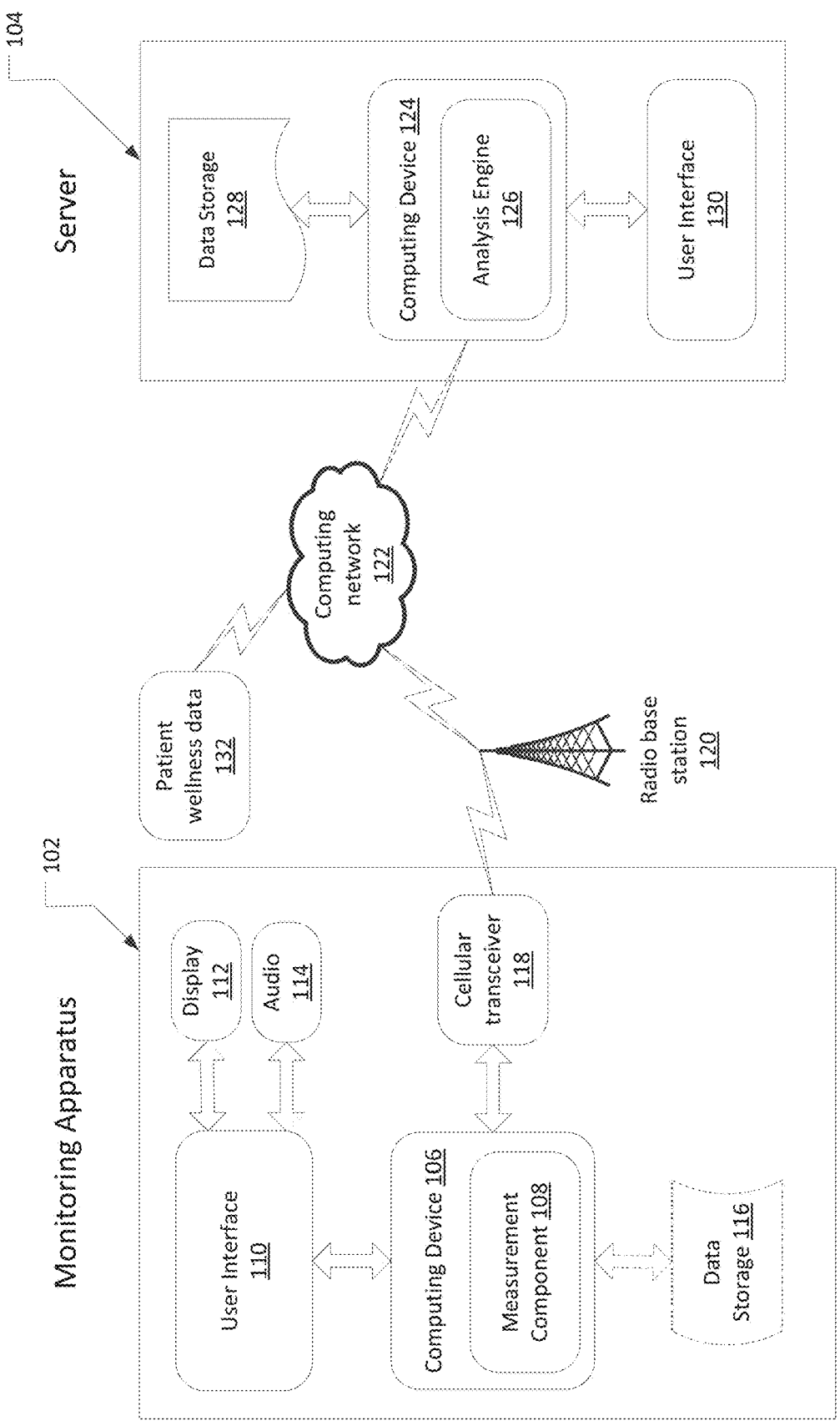
FIG. 2 is an illustration of an embodiment of a suitable monitoring apparatus having an integrated cellular transceiver for relaying patient data.

FIG. 2 is an illustration of an embodiment of a monitoring apparatus 102 having an integrated cellular transceiver 118 for relaying patient data.

The monitoring device 102 is one embodiment of a monitoring apparatus (i.e., monitoring apparatuses 14*a*-*d*) in the plurality of monitoring apparatuses 14. The monitoring device 102 and remote processing system 104 may comprise various computing modules, sub-modules, components, etc., for measuring, transmitting, storing, and analyzing patient data. Indeed, functional steps, operations, methods, etc., as described herein may be conducted by any suitable combination of hardware and software on monitoring apparatus 102 or remote processing system 104. The remote processing system 104 is one embodiment of the remote processing system 18 of FIG. 1.

Though it is not shown, it is understood that in alternative embodiments, multiple servers/processing systems similar to remote processing system 104 may exist at various remote locations. In some embodiments, the multiple servers may communicate with each other so that data sent to one server is evaluated in conjunction with data sent to another server. The monitoring device 102 may determine which server to send patient health data to depending on various factors including whether particular servers are busy, non-operational, or the like.

Figure 3:
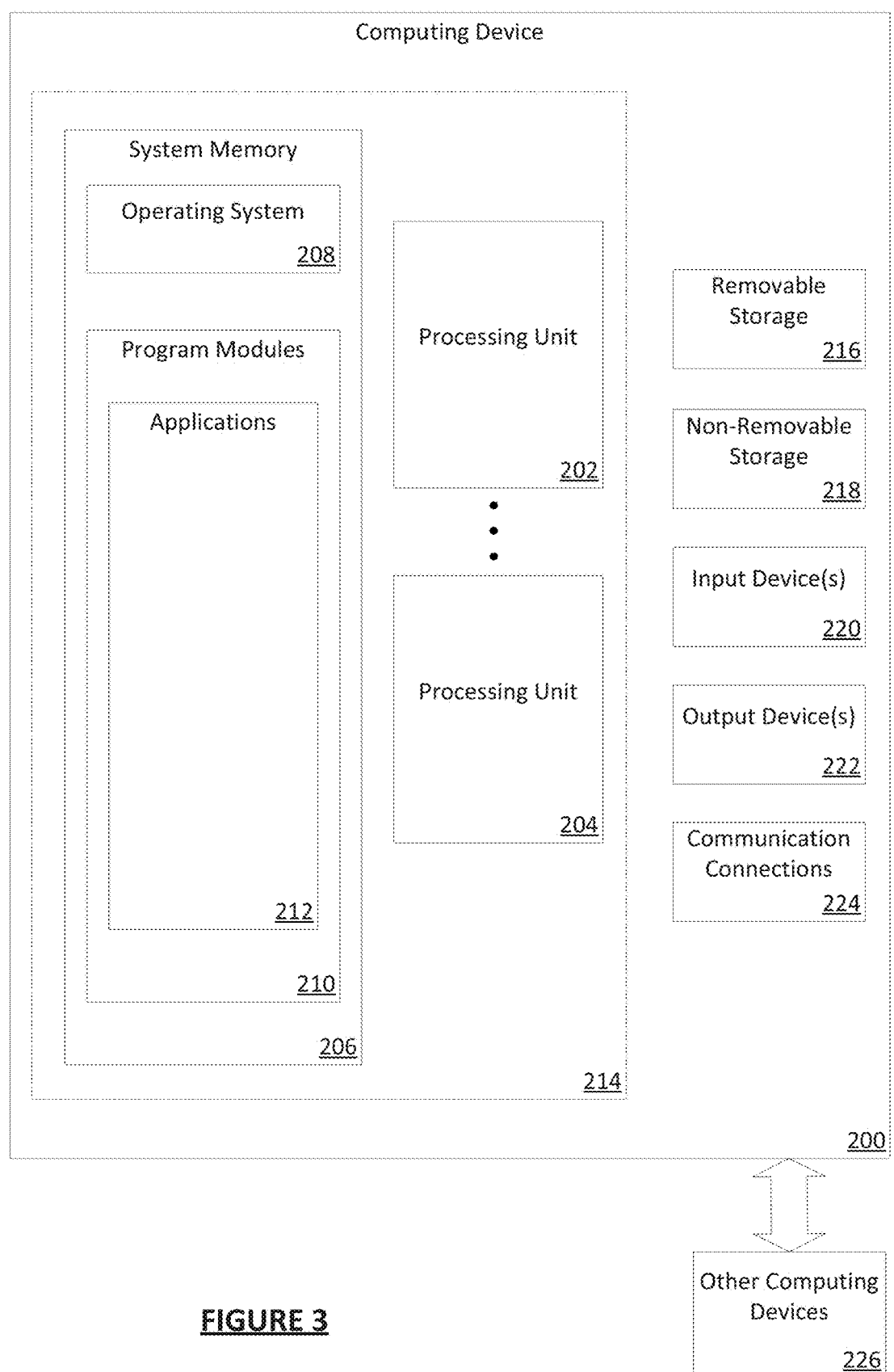
FIG. 3 is a block diagram illustrating an embodiment of a suitable computer system for implementing one or more aspects of the present disclosure.

For example, monitoring apparatus 102 may include a computing device 106 (e.g., computing device 200 illustrated in FIG. 3). Computing device 106 may include at least one processing unit and a system memory and may be any suitable computing device configured to receive, store, and/or transmit patient data.

According to embodiments, computing device 106 may be in communication with measurement component 108. According to embodiments, measurement component 108 is an electronic scale having one or more of the following elements: load cells, pressure transducers, linear variable differential transformers (LVDTs), capacitance coupled sensors, strain gages, and semiconductor strain gages. In alternative embodiments, the measurement component 108 may be a blood pressure device configured to detect a blood saturation level for the patient without requiring blood samples. In other embodiments, the measurement component 108 may be a pulse oximeter configured to detect a blood oxygen saturation level for the patient without requiring blood samples. In yet alternative embodiments, the measurement component 108 may be a blood pressure reading device.

According to embodiments, these devices convert a patient's measurement into a useable electronic signal that is representative of the patient's measured parameter. According to further embodiments, the electronic signal may be associated with a time stamp indicating the time that the parameter was measured by measurement component 108. According to still further embodiments, the electronic signal may be associated with an identifier corresponding to the monitoring apparatus 102 and/or the patient.

The computing device 106 may further be in communication with user interface 110. According to embodiments, user interface 110 enables a user to communicate with monitoring apparatus 102. That is, user interface 110 may be configured for accepting input and/or providing output. According to additional embodiments, user interface 110 may be in communication with a display device, e.g., display device 112. For example, user interface 110 may be configured to accept input via display device 112. In some embodiments, user interface 110 may provide a graphical user interface (GUI) via display device 112. Additionally or alternatively, user interface 110 may display information via display device 112. For example, user interface 110 may display output received from measurement component 108, e.g., a patient weight. According to embodiments, information displayed by user interface 110 comprises one or more of: patient parameter data, a prompt, an error, etc.

According to embodiments, patient parameter data includes any measured or collected data regarding a patient parameter, e.g., a patient weight, a patient blood pressure, a patient blood glucose level, a patient blood oxygen saturation level, etc. According to embodiments, a prompt may include a request to step onto or to wear the measurement component 108, a request to contact a healthcare professional, a reminder to take medication, a notification that a measurement was successfully transmitted, a question to be answered by the patient, etc. According to embodiments, an error may include an indication regarding a malfunction of one or more components of the monitoring apparatus 102.

According to additional embodiments, user interface 110 may be in communication with an audio device, e.g., audio device 114. For example, user interface 110 may be configured to accept input and/or provide output via audio device 114. According to some embodiments, the user interface 110 may receive user input regarding one or more patient parameters via audio device 114. For example, user interface 110 may be configured to perform interactive voice recognition ("IVR") via audio device 114. That is, user interface 110 may receive user input via audio device 114, may process the user input at computing device 106, and may provide an appropriate response. According to embodiments, the appropriate response may be displayed as output via display device 112 and/or audio device 114. More information about the IVR system is discussed below in relation to FIGS. 10 and 11.

Computing device 106 may optionally be in communication with data storage 116. Data storage 116 is displayed with dotted lines in order to illustrate that data storage 116 is optional. That is, in some embodiments, data may be stored at least temporarily at the monitoring apparatus 102, whereas in other embodiments data may be stored at remote processing system 104 or at another suitable data storage location (e.g., remote database, not shown). Data storage 116 may include any suitable volatile or non-volatile, removable storage or non-removable storage (e.g., removable storage 216 and non-removable storage 218 illustrated in FIG. 3) for at least temporarily storing data at the monitoring apparatus 102. For example, data may be stored temporarily before data is transmitted to the server, data may be stored for a period of time after data is transmitted, data may be stored for analysis or computational purposes, etc. According to embodiments, data may comprise patient parameter data, a patient (or monitoring apparatus) identifier, date and time of measurement, etc.

According to embodiments, patient parameter data includes any measured or collected data regarding a patient parameter, e.g., a patient weight, a patient blood pressure, a patient blood glucose level, a patient blood oxygen saturation level, etc. According to embodiments, a patient identifier may be any suitable computer-readable identifier that is unique to a particular patient. Alternatively, a monitoring apparatus identifier may be any suitable computer-readable identifier that is unique to a particular monitoring apparatus. According to embodiments, a particular monitoring apparatus may be associated with a particular patient at a central data-processing facility. In this case, transmission of a patient identifier with patient data is unnecessary because transmission of a monitoring apparatus identifier with patient data is sufficient to associate the particular patient with the patient data at the central data-processing facility.

Furthermore, in some embodiments, particular monitoring apparatuses may be associated with one or more other monitoring apparatuses located in the same local vicinity or associated with the same patient or patient record. In embodiments including a plurality of monitoring apparatuses, the devices may communicate with each other or with the remote processing system 18 about other devices. The devices may communicate with each other for a variety of reasons. For example, if a patient has not measured a certain parameter in a predetermined amount of time, a device located near the blood pressure device may alert the patient to measure his blood pressure. Alternatively, the device may transmit a signal with the blood pressure device to alert the patient to measure his blood pressure. In yet alternative embodiments, monitoring apparatuses may communicate with one another for trouble-shooting purposes. For example, the remote processing system 18 could utilize one device to elicit a response from another device located in proximity to the first device. For such applications, global positioning (GPS) systems may be utilized.

Computing device 106 may also be in communication with cellular transceiver 118. In general, a cellular network is a radio network distributed over a geographic area, or "cell." Geographic cells may be defined via any suitable means, e.g., a hexagonal, square, circular, irregular, or other grid (commonly hexagonal). Each geographic cell is associated with at least one radio base station, which is in a fixed location within the geographic cell and is associated with one or more radio frequencies (e.g., a range of radio frequencies or "channels") for receiving and transmitting radio waves within the geographic cell. To prevent interference, radio base stations located in adjacent geographic cells are generally not associated with the same range of radio frequencies. According to embodiments, each radio base station is further associated, or connected, to a land (or wired) telephone network.

According to embodiments, a cellular modem may combine a data modem and a cellular transceiver for communicating data over a cellular network. A data modem (i.e., modulator-demodulator) is an apparatus that encodes digital data by modulating an analog carrier signal. For example, a data modem may convert digital data (e.g., of a computer) into modulated electrical signals in an appropriate frequency for cellular transmission (e.g., microwave range). According to embodiments, the modulated electrical signals can be transmitted over telephone lines (or via cellular links to telephone lines) and demodulated by another modem at the receiver side to recover the digital data. When the data modem is paired with a cellular transceiver, the modulated electrical signals may be transmitted via a radio base station to an intended radio receiver. According to embodiments, digital data may be transmitted via a number of different digital cellular technologies that are either currently know or may be developed in the future, including: Global System for Mobile Communications (GSM), General Packet Radio Service (GPRS), Code Division Multiple Access (CDMA), Evolution-Data Optimized (EV-DO), Enhanced Data Rates for GSM Evolution (EDGE), 3GSM, Digital Enhanced Cordless Telecommunications (DECT), Digital AMPS (IS-136/TDMA), Integrated Digital Enhanced Network (iDEN), etc.

According to some embodiments, cellular transceiver 118 may be a cellular modem and may convert digital data into modulated electrical signals for transmission via radio waves. Digital data may include output from measurement component 108, e.g., a patient weight. Moreover, digital data may include any other suitable data generated or collected by monitoring apparatus 102, e.g., patient parameter data, identification data, etc. Additionally, cellular transceiver 118 may transmit the modulated electrical signals to radio base station 120 via at least one radio frequency (or channel). According to some embodiments, cellular transceiver 118 is integrated into monitoring apparatus 102 via any suitable means. According to other embodiments, cellular transceiver 118 is portable and is in communication with monitoring apparatus 102 via any suitable means (e.g., wired and/or wireless means). According to further embodiments, cellular transceiver 118 may also receive modulated electrical signals, e.g., from remote processing system 104, and may demodulate the modulated electrical signals to recover digital data.

According to other embodiments, another component of the monitoring apparatus 102 may convert digital data into modulated electrical signals suitable for cellular transmission (e.g., an electronic scale). In this case, cellular transceiver 118 may not comprise a data modem and may be configured merely to receive and/or transmit a modulated electrical signal. According to alternative embodiments, the modulated electrical signal generated by the electronic scale may need to be adjusted to an appropriate radio frequency for cellular transmission by a cellular modem associated with the cellular transceiver 118.

According to some embodiments, the modulated electrical signals (representing digital data from monitoring apparatus 102) may be transmitted from the radio base station 120 to a computing network 122. The transmitted modulated electrical signals may be communicated from radio base station 120 to the computing network 122 via one or more additional radio base stations, via one or more wired connections (e.g., telephone lines, digital cable lines, etc.), or via any other suitable means. According to embodiments, computing network 122 may involve a distributed system (e.g., cloud-based computing system), where application functionality, memory, data storage and retrieval and various processing functions may be operated remotely from each other over a distributed computing network, such as the Internet or an intranet. For example, computing network 122 may include, but is not limited to, the Internet, an intranet, a wide area networks (WAN), a local area networks (LAN), and a virtual private network (VPN). In some embodiments, the monitoring apparatus 102 may directly transmit data over computing network 122 without use of the cellular transceiver 118. In yet further embodiments, the monitoring apparatus may switch which network to utilize based on the speed, functionality, and operating conditions of the various networks.

Additionally, according to embodiments, patient wellness data 132 may be transmitted to the computing network 122 via any suitable means. According to embodiments, the patient wellness data 132 may be collected by any suitable component or apparatus. According to some embodiments, patient wellness data 132 is not collected by monitoring apparatus 102. Patient wellness data 132 may include collected and/or compiled data regarding patient responses to wellness questions including, for example: Are you feeling short of breath? Did you awaken during the night short of breath? Did you need extra pillows last night? Are you coughing more than usual? Are your ankles or feet swollen? Does your stomach feel bloated? Do you feel dizzy or lightheaded? Are you more tired than usual? Are you taking your medication? Has your appetite decreased? Are you reducing your salt intake? Did you exercise today?

The computing network 122 may be in communication with remote processing system 104. For example, in an embodiment the remote processing system 104 has access to computing network 122 via some suitable network connection, e.g., a private (secured) or a public (unsecured) network connection, a wired or a wireless network connection, etc. The remote processing system 104 may receive digital data from monitoring apparatus 102 or may transmit digital data to monitoring apparatus 102 via computing network 122. The digital data may be received as a modulated electronic signal and remote processing system 104 may demodulate the modulated electronic signal to retrieve the digital data. According to other embodiments, the modulated electronic signal may be demodulated by one or more computing systems associated with computing network 122 and remote processing system 104 may directly retrieve the digital data from computing network 122. The digital data received by remote processing system 104 may include patient parameter data transmitted from monitoring apparatus 102, patient wellness data 132, identification data, etc.

According to embodiments, remote processing system 104 may include a computing device 124 (e.g., computing device 200 illustrated in FIG. 2). Computing device 124 may include at least one processing unit and a system memory. For example, computing device 124 may be any suitable computing device for receiving, storing, and/or transmitting patient data.

Computing device 124 may be in communication with an analysis engine 126. Analysis engine 126 may be a component or module of computing device 124, e.g., a software application or other computer-readable logic, for analyzing, compiling, scoring, ranking, evaluating, or otherwise, the received digital data. For example, analysis engine 126 may be operative to determine a patient wellness score(s) based on received digital data for a particular patient, e.g., patient parameter data, patient wellness data, identification data, etc. For example, the analysis engine 126 may calculate one or more scores based on information received from the monitoring apparatus 102. For example, an individual score for each symptom and/or condition may be determined. Alternatively or additionally, the analysis engine 126 may determine an overall health status score indicative of the patient's general health. The analysis engine 126 may utilize information from more than one monitoring apparatus 102 in calculating the score(s). It is understood that the scores may alternatively or additionally be calculated at one or more of the monitoring devices 14. In some embodiments, the remote processing system 104 may transmit data received from the multiple sources of data to one of the monitoring devices 14 to calculate the score(s).

The calculated score(s) may be compared with threshold values to determine the patient's health with respect to particular symptoms, conditions, or general health status. The threshold values may be stored in a data structure within the data storage device 128. The data structure may be a database, look-up table, list, matrix, or the like. The computing device 124 may access the data structure to determine the appropriate threshold values to compare with the calculated score(s).

Based on the calculated score(s), computing device 124 determines further actions. For example, the computing device 124 may determine to take additional patient measurements, prompt secondary health-related question hierarchies to the patient 22, and/or notify the health care professional 24. If the computing device 124 determines to take further patient measurements or prompt additional questions, the computing device 124 may cause the monitoring apparatus 102 to initiate a communication session with the patient 22. In some embodiments, the computing device 124 may determine a time period during which the monitoring apparatus 102 will be triggered to automatically initiate a communication session with the patient 22. If the patient 22 does not transmit requested data during the time period, for example, the computing device 124 may initiate further communication sessions with the patient 22 via the monitoring apparatus 102 and/or alert the health care professional 24 of the patient's absence. The remote processing system 104 may track the time period at the computing device 124 via a timer or the like. For example, based on the score(s), the computing device 124 may start or reset a timer during which further data must be transmitted from the monitoring apparatus 102 to the remote processing system 104. It is understood that in some examples, the computing device 106 within the monitoring apparatus 102 calculates a score or scores based on collected patient data instead of the computing device 124.

Computing device 124 may be in communication with data storage 128. Data storage 128 may include any suitable volatile or non-volatile, removable or non-removable storage (e.g., removable storage 216 and non-removable storage 218 illustrated in FIG. 2) for storing data at the remote processing system 104. Alternatively, data may be stored at some other suitable data storage location (e.g., remote database, not shown).

Computing device 124 may also be in communication with user interface 130. According to embodiments, similar to user interface 110, user interface 130 may enable a user to communicate with remote processing system 104. For example, user interface 130 may be configured for accepting input and/or providing output. For example, user interface 130 may be configured to accept input via one or more input devices, e.g., a keyboard, a mouse, a pen, an audio input device, a touch input device, or other suitable interactive device. According to additional embodiments, user interface 130 may be in communication with a display device (not shown). According to embodiments, user interface 130 may display data received from analysis engine 126 and/or monitoring apparatus 102.

According to some embodiments, a user may evaluate displayed data and perform one or more actions based on evaluating the data. For example, the user may alert a local medical caregiver to take further action regarding the medical care of the patient. Alternatively, the user may provide a report to a local medical caregiver regarding the patient's medical condition, including raw, summarized, scored and/or otherwise manipulated patient parameter data, patient wellness data, patient wellness score data, etc. According to some embodiments, the user is a remote medical caregiver who, upon evaluating the displayed data, determines an appropriate action with respect to the medical care of the patient. For example, the remote medical caregiver may telephone the patient to discuss, clarify, or validate patient wellness and/or patient parameter data. Alternatively, the remote medical caregiver may contact a local medical caregiver who may provide direct patient care to the patient.

As should be appreciated, the particular components of the monitoring apparatus and server system described herein are not exclusive and, as will be understood by those skilled in the art, the particular components as described herein are not intended to limit the system, i.e., additional components may be added, some disclosed components may be excluded and/or disclosed components may be combined in a different arrangement without departing from the spirit of the present disclosure.

FIG. 3 is a block diagram illustrating an embodiment of a suitable computer system for implementing one or more aspects of the present disclosure.

According to embodiments, computing device components described below may be suitable for the computing devices described above. In a basic configuration, the computing device 200 may include one or more processing units 202, 204 and a system memory 206. Depending on the configuration and type of computing device, the system memory 206 may comprise, but is not limited to, volatile storage (e.g., random access memory), non-volatile storage (e.g., read-only memory), flash memory, or any combination thereof. The system memory 206 may further include an operating system 208, one or more program modules 210, which are suitable for running one or more applications 212. The operating system 208, for example, may be suitable for controlling the operation of the computing device 200. This basic configuration is illustrated in FIG. 3 by those components within a dashed line 214.

The computing device 200 may have additional features or functionality. For example, the computing device 200 may also include additional data storage devices (removable and/or non-removable) such as, for example, magnetic disks, optical disks, or tape. Such additional storage is illustrated in FIG. 3 by a removable storage device 216 and a non-removable storage device 218.

A number of program modules and data files may be stored in the system memory 206. While executing on the processing unit(s) 202 and/or 204, the program modules 210 may perform processes including, for example, one or more of the stages of the methods described herein. The aforementioned process is an example, and the one or more processing units 202 and/or 204 may perform other processes. Other program modules that may be used in accordance with embodiments of the present disclosure may include electronic mail and contacts applications, word processing applications, spreadsheet applications, database applications, slide presentation applications, drawing or computer-aided application programs, etc.

Generally, consistent with embodiments of the present disclosure, program modules may include routines, programs, components, data structures, and other types of structures that may perform particular tasks or that may implement particular abstract data types. Moreover, embodiments of the present disclosure may be practiced with other computer system configurations, including hand-held devices, multiprocessor systems, microprocessor-based or programmable consumer electronics, minicomputers, mainframe computers, and the like. Embodiments of the present disclosure may also be practiced in distributed computing environments where tasks are performed by remote processing devices that are linked through a communications network. In a distributed computing environment, program modules may be located in both local and remote memory storage devices.

Embodiments of the present disclosure, for example, may be implemented as a computer process (method), a computing system, or as an article of manufacture, such as a computer program product or computer readable media. The term computer-readable media as used herein may include computer storage media. Computer storage media includes non-transitory, volatile and nonvolatile, removable and non-removable media implemented in any method or technology for storage of information, such as computer-readable instructions, data structures, program modules, or other data. The system memory 206, the removable storage device 216, and the non-removable storage device 218 are all computer storage media examples (i.e., memory storage). Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by the computing device 200. Any such computer storage media may be part of the computing device 200. The computing device 200 may also have one or more input device(s) 220 such as a keyboard, a mouse, a pen, a sound input device, a touch input device, etc. The output device(s) 222 such as a display, speakers, a printer, etc. may also be included. The aforementioned devices are examples and others may be used.

The term computer-readable media as used herein may also include communication media. Communication media may be embodied by computer readable instructions, data structures, program modules, or other data in a modulated data signal (or a modulated electronic signal), such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The computing device 200 may include one or more communication connections 224 (e.g., cellular transceiver 118 as illustrated in FIG. 2) allowing communications with other computing devices 226 (e.g., communication between monitoring apparatus 102 and remote processing system 104 as illustrated in FIG. 2). Examples of suitable communication connections 224 include, but are not limited to, a cellular modem; cellular transceiver; RF transmitter, receiver, and/or transceiver circuitry; universal serial bus (USB); parallel or serial ports; and other connections appropriate for use with the applicable computer readable media.

As should be appreciated, the particular components of the computing device 200 described herein are not exclusive and, as will be understood by those skilled in the art, the particular components as described herein are not intended to limit the system, i.e., additional components may be added, some disclosed components may be excluded and/or disclosed components may be combined in a different arrangement without departing from the spirit of the present disclosure.

Figure 4:
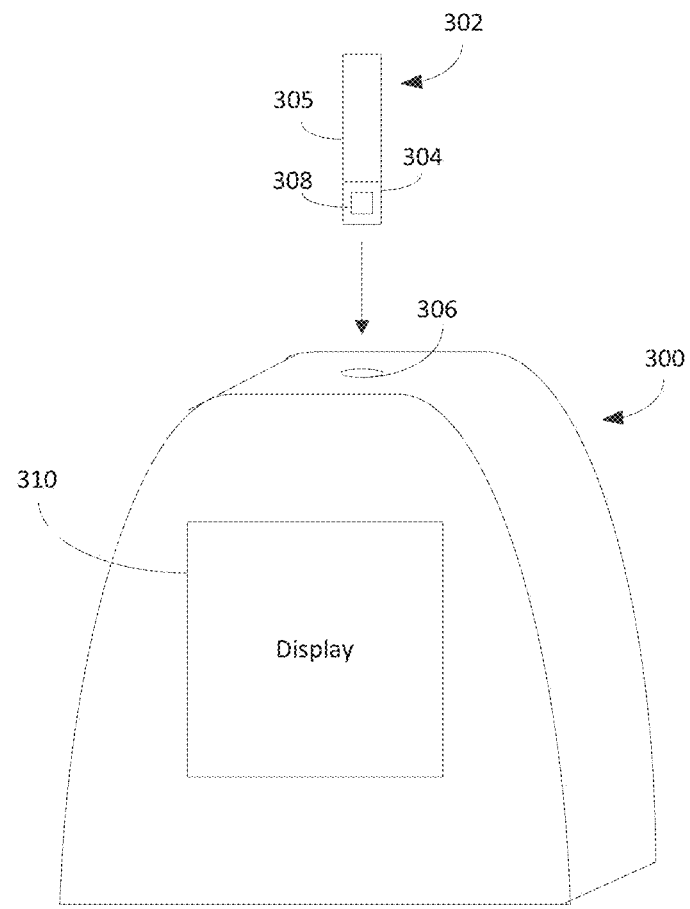
FIG. 4 is an illustration of one embodiment of a suitable monitoring apparatus for implementing one or more aspects of the present disclosure.

FIG. 4 is an illustration of one embodiment of a monitoring apparatus for implementing one or more aspects of the present disclosure.

According to embodiments, a glucometer 300 is shown according to a possible embodiment. The glucometer 300 is one example of a monitoring apparatus in the plurality of monitoring apparatuses 14 of FIG. 1. The glucometer 300 is configured to accept a test strip 302. The test strip 302 has an insertion portion 304 and an exposed portion 305. The insertion portion is placed into an opening 306 in the glucometer 300. According to some embodiments, the insertion portion 304 includes a calibration code, shown as calibration identifier 308, printed along the length of the test strip 302. When the test strip 302 is inserted into the opening 306, the glucometer 300 reads the calibration identifier 308.

According to some embodiments, the calibration identifier 308 is a bar code, and can be read, for example, with an infrared bar code reader. The bar code represents a code that is used to calibrate the glucometer 300 with respect to the particular properties of the test strip 302.

According to further embodiments, the calibration identifier 308 is an integrated circuit or other miniaturized memory device embedded in the test strip and the test strip has leads that are electrically connected to the internal circuitry of the glucometer 300, allowing the glucometer 300 to read the memory embedded in calibration identifier 308 and correspondingly calibrate the meter 300. In such an embodiment, it is understood that the integrated circuit or miniaturized memory device itself need not be included on the insertion portion 304; rather, an interface to the integrated circuit will be included on the insertion portion so as to interface with the glucometer 300.

Glucometers, such as glucometer 300 can determine the blood glucose level of a patient by comparing a measured voltage, resistance, current, or other circuit value sensed in the test strip with known quantities. For example, the glucometer 300 can use a look-up table stored in memory to determine the accurate blood glucose concentration. The glucometer 300 could alternately calculate the blood glucose concentration.

Generally, before a patient uses glucometer 300, that patient needs to calibrate the meter to the test strips 302. This calibration should be done every time a new container of test strips is opened and before the first strip is used. This is because each batch of test strips, and potentially each test strip within a given batch, has varying characteristics that can change the performance of the strip (i.e. there is a proportional difference in glucose detected based on the amount of hexokinase or other chemical on the strip). Some meters require that the patient push a button until the number that appears on the display corresponds to the number located on the test strip container. Other meters use strips that come with an encoded key or strip that allow patients to calibrate the meter by inserting the encoded key or strip into a slot in the meter. By providing a calibration identifier 308 on each test strip 302, accurate and reliable calibration is achieved automatically upon insertion of each test strip, eliminating the need for a separate calibration strip, a calibration chip, or manual code entry by a patient.

The glucometer 300 further includes a display 310 (e.g., display device 112 illustrated in FIG. 2). The display 310 may present test results to a patient once a sample is read by the meter 300. The display 310 can also present a variety of messages to the patient related to the insertion of a test strip 302 and calibration of the meter 300. Additionally or alternatively, display 310 may provide output received from measurement component 108, e.g., a patient blood glucose reading. According to embodiments, information presented by display 310 comprises one or more of: patient parameter data, a prompt, an error, etc. According to embodiments, patient parameter data includes any measured or collected data regarding a patient parameter, e.g., a patient blood glucose level. According to embodiments, a prompt may include a request to insert a test strip into the glucometer 300, a request to contact a healthcare professional, a reminder to take medication, an indication that a patient blood glucose reading was successfully transmitted, etc. According to embodiments, an error may include an indication regarding a malfunction of one or more components of the glucometer 300, an indication that a patient glucose level is outside of an acceptable range (i.e., likely an inaccurate reading), etc.

In some embodiments, the display 310 may inform the patient about the patient's measurements. Furthermore, the display 310 may exhibit general educational information relevant to the patient, such as what the patient should not be eating or other like information or medical feedback. Alternatively, if a person other than the patient is using the medical apparatus, the display 310 may inform the user that the glucometer 300 is only meant for use by the patient. This may be determined by the glucometer 300 by significant changes in measured parameters in over a predetermined amount of time, such as, for example, one day. In yet further embodiments, all of the messages and information displayed on display 310 may be outputted through an output device (not shown) so that the patient may hear the information.

As should be appreciated, the particular embodiments of the monitoring apparatus 300 described herein are not exclusive and, as will be understood by those skilled in the art, the particular embodiments as described herein are not intended to limit the system, but to provide examples of suitable embodiments of a monitoring apparatus within the spirit of the present disclosure.

Figure 5:
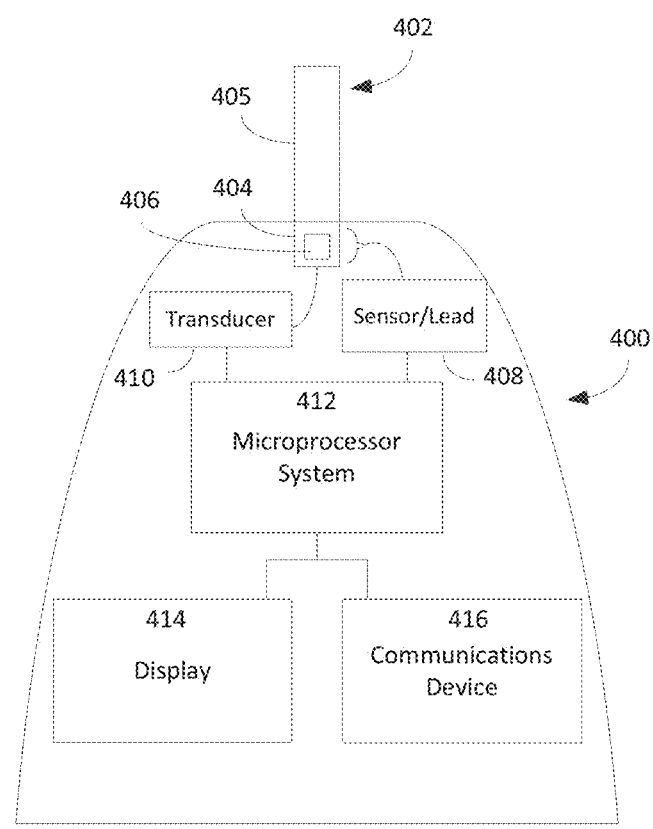
FIG. 5 is an illustration of another embodiment of a suitable monitoring apparatus for implementing one or more aspects of the present disclosure.

FIG. 5 is a block diagram of internal circuitry according to an embodiment of a glucometer 400.

In the embodiment shown, a test strip 402 includes an insertion portion 404 and an external portion 405. The test strip 402 can be inserted into the glucometer 400 such that the insertion portion 404 resides within the glucometer 400. A calibration identifier 406 located on the insertion portion 404 is interfaced with a calibration identifier access device, shown as sensor 408.

According to embodiments, the test strip 402 is also interfaced with a transducer 410, which detects the level of glucose in the blood sample on the test strip and converts that reading to an electrical signal representative of such a sample.

According to further embodiments, both the transducer 410 and a sensor 408 are interfaced with a microcontroller system 412 (e.g., as illustrated with respect to computing device 200 in FIG. 3). Hence, when the microcontroller system 412 receives the signal from the sensor 408 (e.g., such as measurement component 108 as illustrated in FIG. 2), the system 412 can use the resultant signal to selfcalibrate and produce accurate results based on the electrical signal produced by the transducer 410 as read from the test strip 402.

According to further embodiments, the microcontroller system 412 is operatively connected to a display 414 and a communications device 416 (e.g., cellular transceiver 118 as illustrated in FIG. 2). The display 414 can be any type of liquid crystal, diode, or other display capable of low power production of a signal for communication to a patient. According to embodiments, information presented by display 414 comprises one or more of: patient parameter data (e.g., a blood glucose reading), a prompt, an error, etc.

In some embodiments, the glucometer 400 may internally store a set of firmware. The firmware may include a set of computer-executable instructions. When the microprocessor system 412 executes the instructions, they may cause the glucometer 400 to download a dataset from a monitoring server, such as the remote processing system 18, via a network, such as the network 20. The dataset may include one or more prompts. The prompts, when executed, may cause the glucometer 400 to execute a portion of the firmware which causes the glucometer 400 to present: one or more questions to the patient, statements that request a patient response, requests for the patient to utilize a device that measures a physiological characteristic of the patient, and other such information. In addition, the prompts in a dataset may include sets of instructions that cause the microprocessor system 412 to execute instructions stored in firmware that cause the glucometer 400 to automatically gather blood glucose measurements of the patient. Further, the prompts in a dataset may include sets of instructions that cause the microprocessor system 412 to automatically initiate health monitoring sessions with the patient, communicate with the patient, and/or communicate with other health monitoring apparatuses in the system. The prompts may also include sets of instructions that cause the microprocessor system 412 to upload and download information to and from other health monitoring apparatuses (e.g., monitoring apparatuses 14) in the system and/or the remote processing system.

Figure 6:
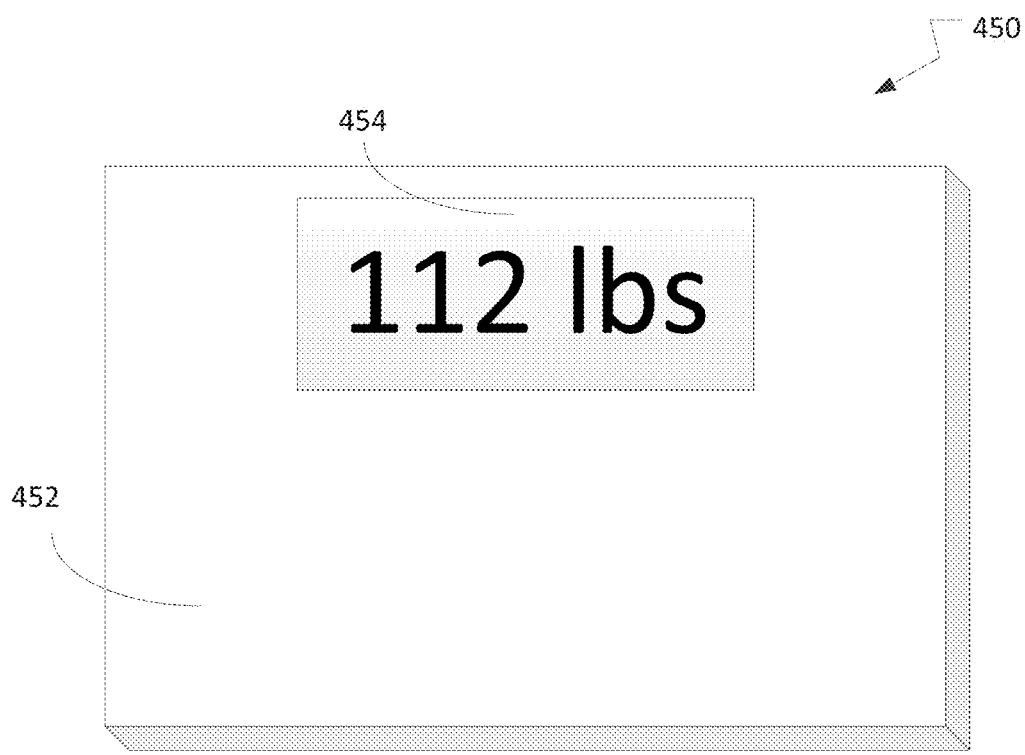
FIG. 6 is an illustration of one embodiment of internal circuitry according to an embodiment of the suitable monitoring apparatus of FIG. 4.

FIG. 6 is an illustration of an electronic scale monitoring apparatus 450.

In FIG. 6, the monitoring apparatus 450 (e.g., monitoring apparatus 102 as illustrated in FIG. 2) is an electronic scale that may utilize any suitable technology for measuring a patient weight. For example, the monitoring apparatus 450 may comprise one or more of the following elements: load cells, pressure transducers, linear variable differential transformers (LVDTs), capacitance coupled sensors, strain gages, and semiconductor strain gages. According to embodiments, the scale 450 may convert a patient's weight into a useable electronic signal that is representative of the patient's weight. The electronic signal may include or be associated with a time stamp indicating the time that the weight was measured by the scale 450. According to still further embodiments, the electronic signal may be associated with an identifier corresponding to the scale 450 and/or the patient.

According to embodiments, the scale 450 may further comprise a surface 452 upon which a patient stands so that a measurement may be taken. Scale 450 may further comprise a display 454 (e.g., such as display 112 as illustrated in FIG. 2) for displaying output, e.g., patient parameter data, a prompt, an error, etc. In some embodiments, the display 454 may act similarly to the display 310, discussed above. Furthermore, an output device (not shown) may alternatively or additionally audibly present messages/alerts to the patient.

According to further embodiments, scale 450 may comprise a cellular transceiver (as shown in FIG. 2). As discussed above, the cellular transceiver may include a data modem for converting a patient weight, as measured by the scale 450, into a modulated electrical signal suitable for cellular transmission. According to further embodiments, the cellular transceiver is configured to receive and/or transmit a modulated electrical signal that is representative of a patient's weight. In other embodiments, the cellular transceiver is configured to receive and/or transmit modulated electrical signals indicative of patient responses to questions relating to the patient's health, information about other wellness parameters, and general health educational information that can later be presented to the patient.

The scale 450 may internally store a set of firmware. The firmware may include a set of computer-executable instructions. When the scale 450 executes the instructions, they may cause the scale 450 to download a dataset from a monitoring server, such as the remote processing system 18, via a network, such as the network 20. The dataset may include one or more prompts. The prompts, when executed, may cause the scale 450 to execute a portion of the firmware which causes the scale 450 to present: one or more questions to the patient, statements that request a patient response, requests for the patient to utilize a device that measures a physiological characteristic of the patient, and other such information. In addition, the prompts in a dataset may include sets of instructions that cause the microprocessor system 412 to execute instructions stored in firmware that cause the scale 450 to automatically gather weight measurements of the patient. Further, the prompts in a dataset may include sets of instructions that cause the scale 450 to automatically initiate health monitoring sessions with the patient, communicate with the patient, and/or communicate with other health monitoring apparatuses in the system. The prompts may also include sets of instructions that cause the scale 450 to upload and download information to and from other health monitoring apparatuses (e.g., monitoring apparatuses 14) in the system and/or the remote processing system.

Figure 7:
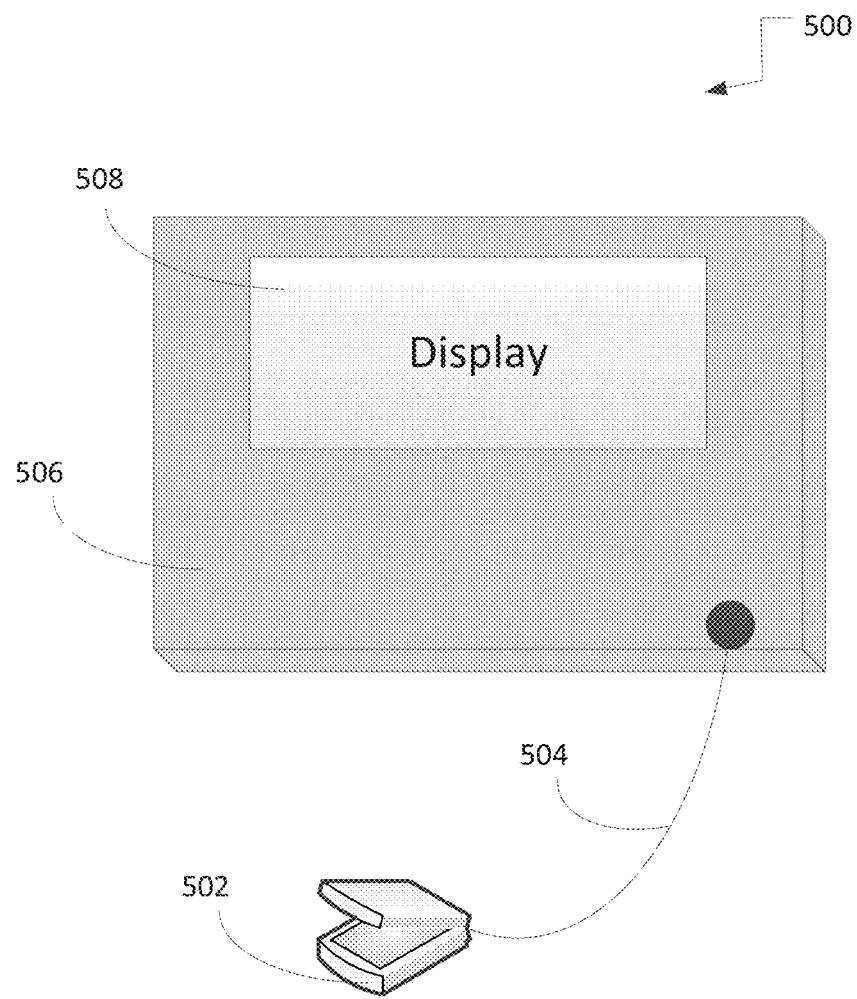
FIG. 7 is an illustration of another embodiment of a suitable monitoring apparatus for implementing one or more aspects of the present disclosure.

FIG. 7 is an illustration of an oximeter monitoring apparatus 500.

According to embodiments, the monitoring apparatus 500 comprises an oximetry sensor 502 (e.g., measurement component 108 as illustrated in FIG. 2) that is configured to indirectly monitor an oxygen saturation of a patient's blood by monitoring the patient's skin. The oximetry sensor 502 may be configured to monitor the skin of a patient's finger. That is, oximetry sensor 502 may measure a patient's heart rate and/or blood oxygen level without requiring a blood sample. According to embodiments, oximetry sensor 502 is communicatively coupled to the monitoring apparatus 500 via one or more leads 504.

According to embodiments, the monitoring apparatus 500 further comprises a body 506 and a display 508. For example, display 508 (e.g., display device 112 illustrated in FIG. 2) may present a patient blood oxygen saturation reading to a patient upon receiving a measurement from oximetry sensor 502. According to some embodiments, monitoring apparatus 500 may generate a report, referred to as a photoplethysmogram, which provides a trend of the patient's blood oxygen saturation over time. According to embodiments, the photoplethymogram may be displayed on display 508. In some embodiments, the display 508 may act similarly to the display 310, discussed above. Furthermore, an output device (not shown) may alternatively or additionally audibly present messages/alerts to the patient. According to additional or alternative embodiments, the photoplethymogram may be transmitted to a remote, central data-processing facility or server. According to further embodiments, the monitoring apparatus 500 comprises a cellular transceiver (not show) as described in above embodiments.

The monitoring apparatus 500 may internally store a set of firmware. The firmware may include a set of computer-executable instructions. When the monitoring apparatus 500 executes the instructions, they may cause the monitoring apparatus 500 to download a dataset from a monitoring server, such as the remote processing system 18, via a network, such as the network 20. The dataset may include one or more prompts. The prompts, when executed, may cause the monitoring apparatus 500 to execute a portion of the firmware which causes the apparatus 500 to present: one or more questions to the patient, statements that request a patient response, requests for the patient to utilize a device that measures a physiological characteristic of the patient, and other such information. In addition, the prompts in a dataset may include sets of instructions that cause the monitoring apparatus 500 to execute instructions stored in firmware that cause the monitoring apparatus 500 to automatically gather wellness and health measurements of the patient. Further, the prompts in a dataset may include sets of instructions that cause the monitoring apparatus 500 to automatically initiate health monitoring sessions with the patient, communicate with the patient, and/or communicate with other health monitoring apparatuses in the system. The prompts may also include sets of instructions that cause the monitoring apparatus 500 to upload and download information to and from other health monitoring apparatuses in the system and/or the remote processing system.

Figure 8:
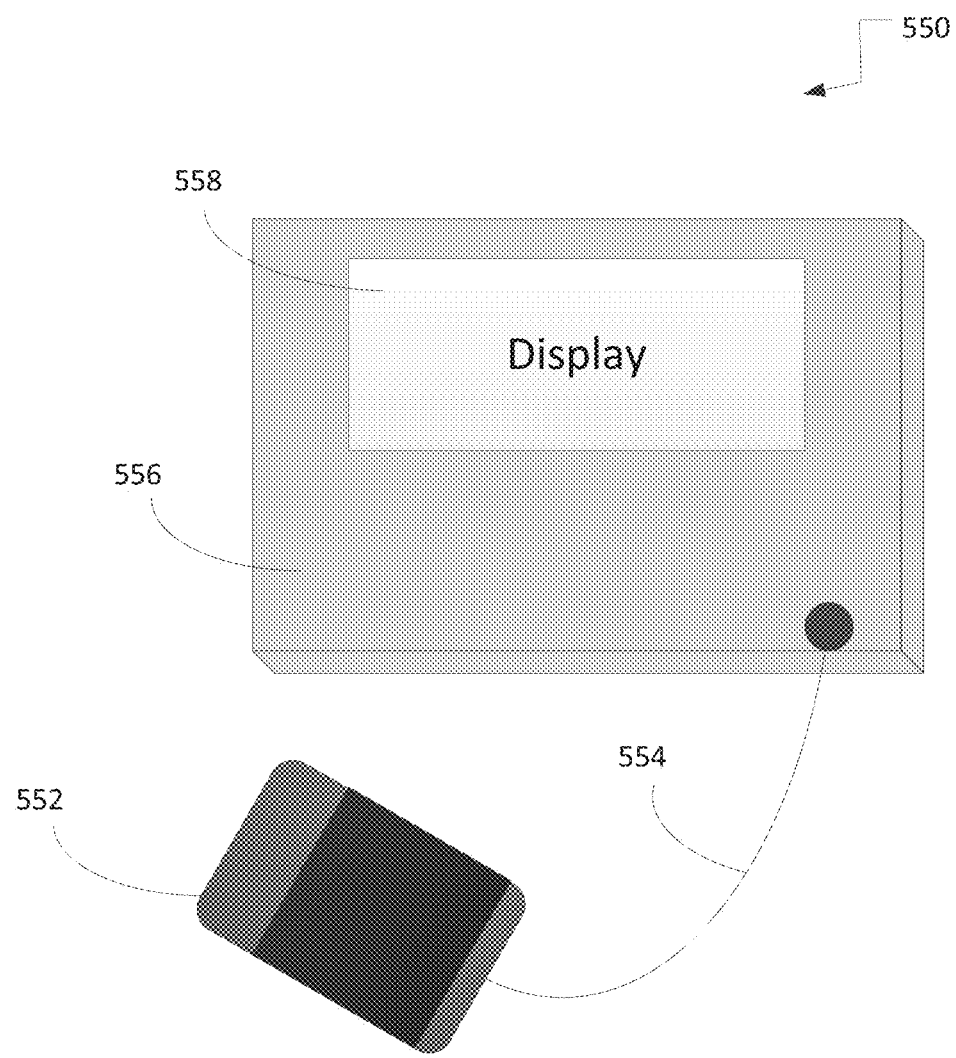
FIG. 8 is an illustration of another embodiment of a suitable monitoring apparatus for implementing one or more aspects of the present disclosure.

FIG. 8 is an illustration of yet another embodiment of a monitoring apparatus 550 for implementing one or more aspects of the present disclosure.

According to embodiments, the monitoring apparatus 550 comprises a blood pressure cuff 552 (e.g., measurement component 108 as illustrated in FIG. 2) that is configured to monitor a patient's blood pressure. Generally, a blood pressure cuff is a device used to measure the force of the blood in the veins and arteries. For example, when a patient is at rest, the force of blood flow is generally constant and, in healthy individuals, should range between 110/70 and 120/80. The systolic number (i.e., the greater number) represents the force of blood as the heart contracts. The diastolic number (i.e., the lesser number) represents the force of blood as the heart relaxes. According to embodiments, the blood pressure cuff 552 inflates to restrict blood flow. Thereafter, the blood pressure cuff 552 slowly deflates to resume blood flow.

According to embodiments, the blood pressure cuff 552 is coupled to a suitable pressure transducer (not shown) that measures a pressure when blood flow just resumes as the blood pressure cuff is deflating and a pressure when blood flow returns to being unimpeded by the blood pressure cuff. According to embodiments, the pressure transducer may be integrated into the blood pressure cuff 552, integrated into a body 556 of the monitoring apparatus 550, or otherwise communicatively coupled to the blood pressure cuff 552. According to embodiments, blood pressure cuff 552 is communicatively coupled to the monitoring apparatus 550 via one or more leads 554.

According to embodiments, the monitoring apparatus 550 further comprises the body 556 and a display 558. For example, display 558 (e.g., display device 112 illustrated in FIG. 2) may present a patient blood pressure reading to a patient upon receiving a measurement from blood pressure cuff 552 and/or the pressure transducer. In some embodiments, the display 558 may act similarly to the display 310, discussed above. Furthermore, an output device (not shown) may alternatively or additionally audibly present messages/alerts to the patient. According to further embodiments, the monitoring apparatus 550 comprises a cellular transceiver (not show) as described in above embodiments.

The monitoring apparatus 550 may internally store a set of firmware. The firmware may include a set of computer-executable instructions. When the monitoring apparatus 550 executes the instructions, they may cause the monitoring apparatus 550 to download a dataset from a monitoring server, such as the remote processing system 18, via a network, such as the network 20. The dataset may include one or more prompts. The prompts, when executed, may cause the monitoring apparatus 550 to execute a portion of the firmware which causes the apparatus 550 to present: one or more questions to the patient, statements that request a patient response, requests for the patient to utilize a device that measures a physiological characteristic of the patient, and other such information. In addition, the prompts in a dataset may include sets of instructions that cause the monitoring apparatus 550 to execute instructions stored in firmware that cause the monitoring apparatus 550 to automatically gather wellness and health measurements of the patient. Further, the prompts in a dataset may include sets of instructions that cause the monitoring apparatus 550 to automatically initiate health monitoring sessions with the patient, communicate with the patient, and/or communicate with other health monitoring apparatuses in the system. The prompts may also include sets of instructions that cause the monitoring apparatus 550 to upload and download information to and from other health monitoring apparatuses in the system and/or the remote processing system.

As should be appreciated, the particular embodiments of FIGS. 4-8, described herein, are not exclusive and, as will be understood by those skilled in the art, the particular embodiments as described herein are not intended to limit the system, but to provide examples of suitable embodiments of a monitoring apparatus within the spirit of the present disclosure.

Figure 9:
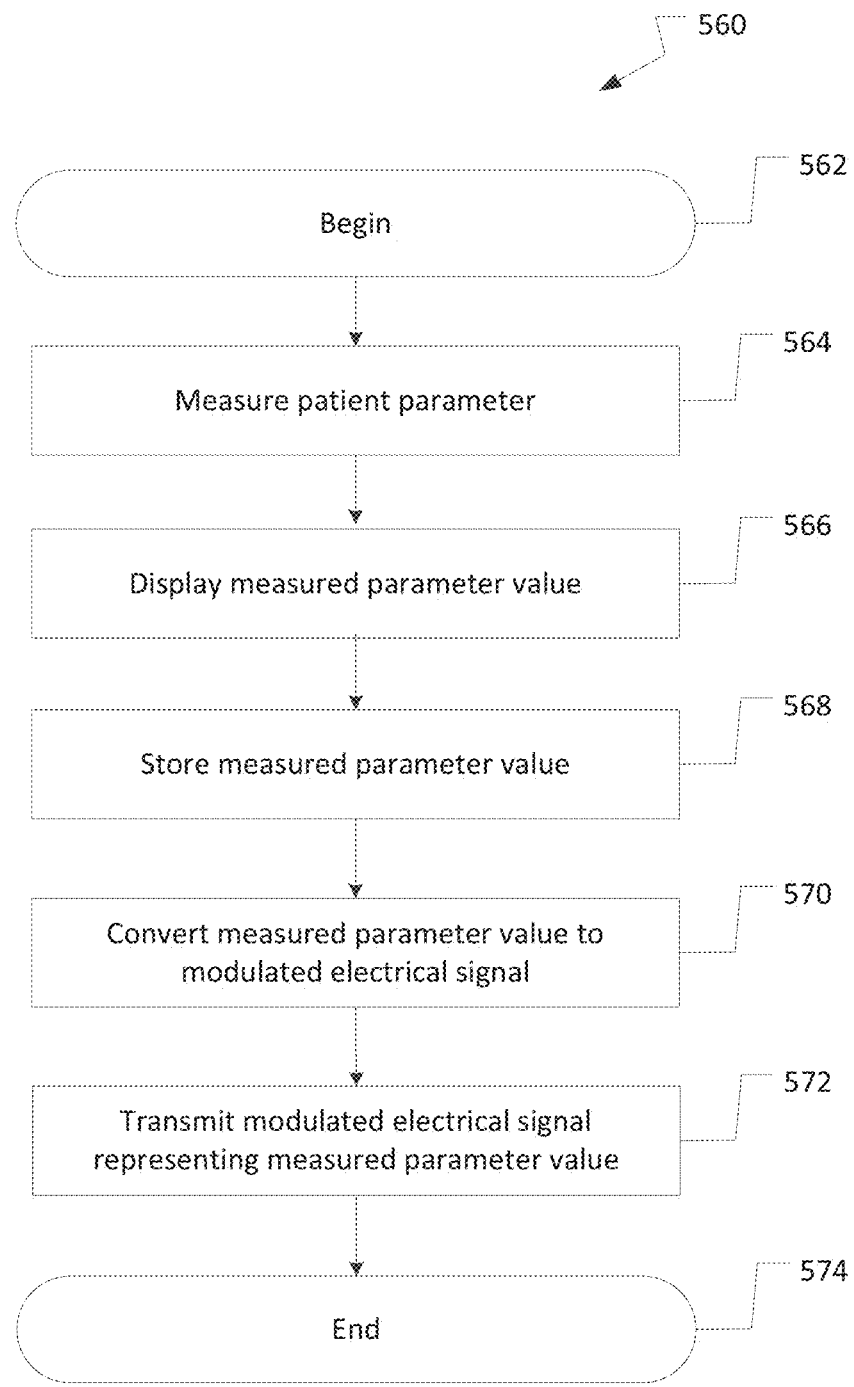
FIG. 9 is a flow diagram representing an embodiment of a method for measuring and transmitting patient data.

FIG. 9 is a flow diagram representing an embodiment of a method 560 for measuring and transmitting patient data. According to some embodiments, some or all of the method of FIG. 9 may be implemented on a monitoring apparatus, e.g., monitoring apparatus 102.

The method of FIG. 9 begins with begin operation 562. Begin operation 562 may refer to any suitable initiation of a method for measuring and transmitting patient data. For example, begin operation 562 may involve a patient stepping on or otherwise initiating a monitoring apparatus to measure the patient's weight.

At measure patient parameter operation 564, a monitoring apparatus may measure a patient parameter, e.g., a patient's weight. For example, the monitoring apparatus may be an electronic scale having one or more of the following elements: load cells, pressure transducers, linear variable differential transformers (LVDTs), capacitance coupled sensors, strain gages, and semiconductor strain gages. According to embodiments, the monitoring apparatus may convert the patient's weight into a useable electrical signal that is representative of the patient's weight. According to further embodiments, the electrical signal may be associated with a time stamp indicating the time that the weight was measured by the monitoring apparatus. According to still further embodiments, the electrical signal may be associated with an identifier corresponding to the monitoring apparatus and/or the patient. According to some embodiments, the electrical signal generated by the electronic scale may be adjusted to an appropriate radio frequency for cellular transmission by a cellular modem, as described below.

At optional display operation 566 (identified by dotted lines), a measured parameter value may be displayed on the monitoring apparatus. For example, the patient's weight may be displayed on the monitoring apparatus via a display device. According to some embodiments, the monitoring apparatus may not be configured with a display device and the measured parameter value may not be displayed on the monitoring apparatus. According to other embodiments, the monitoring apparatus may not display the measured parameter value unless or until a command to display the measured parameter value is received.

At optional store operation 568 (identified by dotted lines), the measured parameter value may be stored by the monitoring apparatus. That is, the monitoring apparatus may comprise suitable memory, e.g., volatile or non-volatile, removable or non-removable storage, for storing the measured parameter value. For example, the measured parameter value may be stored temporarily before the measured parameter value is transmitted (e.g., until a suitable communication session is established), the measured parameter value may be stored for a period of time after the measured parameter value is transmitted (e.g., backup storage), the measured parameter value may be stored for evaluation purposes (e.g., by a local medical caregiver), etc.

At convert operation 570, the monitoring apparatus may convert the measured parameter value into modulated electrical signal. According to some embodiments, the monitoring apparatus may comprise a cellular modem that combines a data modem and a cellular transceiver for communicating data over a cellular network. For example, the cellular modem may convert the measured parameter value into a modulated electrical signal in an appropriate frequency for cellular transmission (e.g., microwave range). According to alternative embodiments, a modulated electrical signal representative of a patient's weight may be generated by another component of the monitoring apparatus (e.g., an electronic scale) and may need to be adjusted to an appropriate radio frequency for cellular transmission by the cellular modem. According to embodiments, the monitoring apparatus may convert a patient weight into a modulated electrical signal in an appropriate frequency for cellular transmission. It is understood, however, that in some examples, the monitoring apparatus may not need to convert the patient parameter into a modulated electrical signal because the monitoring apparatus does not utilize cellular transmission of data.

At transmit operation 572, the monitoring apparatus may transmit a modulated electrical signal representing the measured parameter value. For example, the monitoring apparatus may transmit the modulated electrical signal via a cellular transceiver. According to embodiments, the modulated electrical signal may be transmitted to a central data-processing facility (or server) and may be demodulated by another modem at the receiver side to recover the measured parameter value. For example, the server may demodulate the modulated electrical signal to retrieve a patient weight.

At end operation 574, the method of FIG. 9 may be terminated via any suitable means. For example, end operation 574 may involve completing transmission of the modulated electrical signal and receiving an acknowledgement message from the central data-processing facility or server. According to embodiments, end operation 574 does not in any way prevent conducting begin operation 562 again at some future time.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present disclosure.

Figure 10:
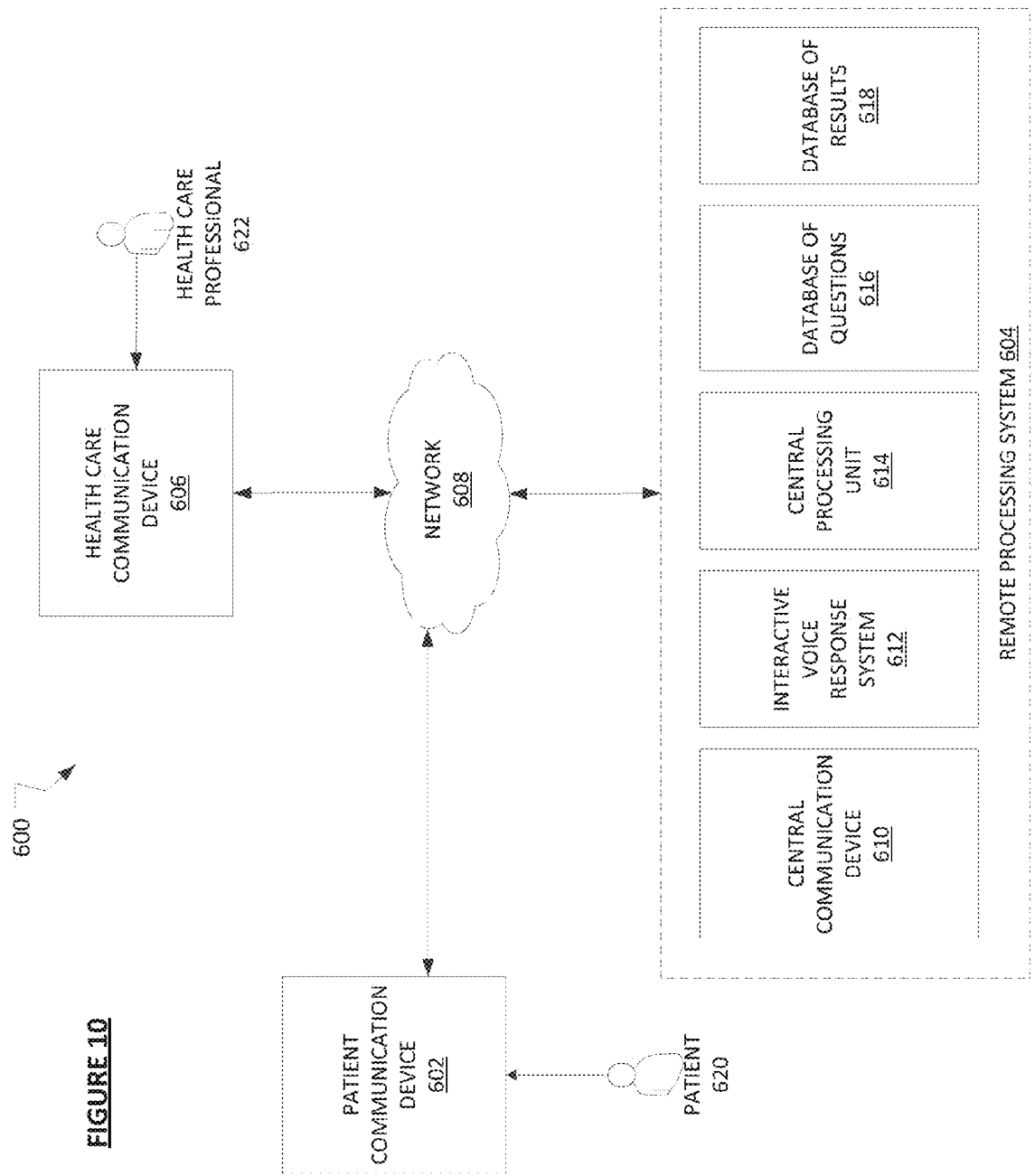
FIG. 10 is a schematic diagram illustrating one embodiment of a patient monitoring system including an interactive voice response system.

FIG. 10 is a schematic diagram illustrating one example of a patient health monitoring system 600 is shown. The patient health monitoring system 600 includes a general-purpose patient communication device 602, remote processing system 604, a health care communication device 606, and a network 608. The remote processing system 604 includes a central communication device 610, an interactive voice response ("IVR") system 612, a central processing unit 614, a database of questions 616, and a database of results 618. The general-purpose patient communication device 602 can be accessed and operated by a patient 620. The health care communication device 606 can be accessed and operated by a health care professional 622. The patient communication device 602, the health care communication device 606, and the network 608 act in the same ways as described above in relation to FIG. 1.

The system 600 is one example of the system 10 (FIG. 1), the communication device 602 is one example of the communication device 12, and the remote processing system 604 is one example of the remote processing system 18. It is understood that, though not shown, the system 600 may include one or more monitoring apparatuses as discussed above, such as, for example, the monitoring apparatuses 14.

The central communication device 610 is located at the remote processing system 604. Examples of the central communication device 620 may include a telephone, a cellular telephone, a pager, a tablet, a computer, or other wireless or wired communication devices. When the patient 620 initiates a communication session with the central communication device 610, the central communication device 610 communicates with the IVR system 612 which interacts with the patient 620 through a series of queries and/or responses based on answers provided by the patient 620.

The IVR system 612 serves as a front end interface through which a caller, such as the patient 620, can access the patient health monitoring system 600. The IVR system 612 acts as other interactive voice response systems that are known in the art. Specifically, the IVR system 612 provides prompts to the patient 620 and receives touch tone and/or spoken responses from the patient 620 in response to the prompts. The IVR system 612 communicates with the central processing unit 614 to determine which queries to present to the patient 620. The central processing unit 614 accesses the database of questions 616 and transmits the questions to the IVR system 612. Upon receiving a response from the patient 620, the IVR system 612 once again communicates with the central processing unit 614, which stores and updates the answers in the database of results 618. Through this series of prompt/response interaction, the IVR system 612 collects sufficient information about the patient 620 to determine a health status of the patient 620.

The central processing unit 614 accesses the database of questions 616 based on the information acquired by the IVR system 612. The database of questions is programmed with several question hierarchies having varying numbers of sets of questions associated with each question hierarchy. In an embodiment, each question hierarchy relates to a symptom condition to be monitored, meaning that the number of question hierarchies stored in the database of questions 616 is dependent upon the number of symptoms that can be monitored. More information relating to the structure of the question hierarchies is discussed in the co-pending patent application entitled, DOWNLOADABLE DATASETS FOR A PATIENT MONITORING SYSTEM, which was previously incorporated by reference herein in its entirety.

The health care communication device 606 may be located at a health care professional's office, health care oversight location, or any other location that is easily accessible to the health care professional 622. The health care professional 622 can access the information gained through the IVR system 612, which is stored in the database of results 618. In some embodiments, the health care professional 622 may be located at the remote processing system 604 and therefore has direct access to the central processing unit 614. In other embodiments, such as that shown in FIG. 10, the health care professional 622 may be located at a different location than the remote processing system 604 and thus may access the central processing unit 614 through the health care communication device 606 by way of the network 608.

In use, the patient 620 may begin interaction with the IVR system 612 through various ways. For example, in one embodiment, the patient 620 may initiate interaction with the IVR system 612 by calling a specific telephone number which connects the patient 620 to the IVR system 612 by way of the network 608. In this example, the network 608 may be a switched telephone network. In another embodiment, the health care professional 622 or some third party may initiate interaction between the patient 620 and the IVR system 612 by prompting the central communication device 610 to call the patient 620. In this example, the patient 620 may choose to interact with the IVR system 612 by answering the call upon receiving it.

In some embodiments, upon initiating interaction with the IVR system 612, the patient 620 may be prompted to input an identification code so that the IVR system 612 can identify the patient 620. The identification code may also be used to ensure that the person engaging with the IVR system 612 is authorized to do so. The patient 620 may input this information either through touch tone (utilizing a dial pad) and/or spoken responses. In some embodiments, the identification code may include a name, unique identification number such as a social security number, or other distinctive number or feature associated with the patient 620 to help the IVR system 612 identify the patient 620. In other embodiments, the IVR system 612 may not prompt the patient 620 for an identification code, but may instead, recognize the telephone number from which the patient 620 is calling, and utilize this telephone number as an identification code.

After identifying the patient 620, the IVR system 612 begins prompting the patient with health-related questions retrieved from the database of questions 618. The method of question prompting is similar to the way in which the monitoring apparatuses 14 (FIG. 1) determine which questions to present to the patient. The patient 620 can respond to the questions either through touch tone and/or spoken responses. The IVR system 612 then transmits the responses from the patient 620 to the central processing unit 614 which updates the database of results 618 with the patient responses. At this time, the central processing unit 614 may calculate or update one or more scores indicative of the patient's health status. The central processing unit 614 then utilizes the responses and/or scores to determine what to present next to the patient 620. For example, in some embodiments, the IVR system 612 may prompt the patient 620 with further questions from the same or different question hierarchies. In other embodiments, the IVR system 612 may present the patient 620 with feedback in response to answers which may include comments on how to improve the patient's health, general statements regarding the patient's health status, teaching tips on how to maintain the patient's health, or the like. In yet other embodiments, the IVR system 612 may complete a question hierarchy and determine (via the central processing unit 614) that no further questions or feedback need to be presented to the patient 620 and therefore terminate the call.

In some embodiments, the remote processing system 604 may utilize data collected from the plurality of monitoring devices 14 to determine whether more information is needed. If more information is desired to properly determine the patient's health score or if one or more scores indicate that a health problem may exist with the patient, the remote processing system 604 may initiate a call to the patient through the IVR system 612 so that it may prompt queries to the patient relevant to the information that the system 604 desires. Additionally, if data from other sources, such as the monitoring apparatuses 14 appear to be incorrect or out of range, the remote processing system 604 may initiate a call to the patient through the IVR system 612 so that it may prompt queries to the patient to ensure that the data collected from the monitoring apparatuses 14 is correct. In some embodiments, if one or more health scores are out of the predetermined threshold, the remote processing system 604 may initiate a call to the patient through the IVR system 612 immediately or within a determined amount of time to collect further health-related data from the patient. If the patient is unresponsive to the call, the remote processing system 604 may try again for a determined amount of times and then notify the health care professional 622.

In some embodiments, the central processing unit 614 may determine that the patient 620 is in need of professional medical assistance. In this case, the IVR system 612 may automatically utilize the central communication device 610 to initiate communication with the health care communication device 606 or send an alert to the health care professional 622 indicating that the patient 620 is in need of medical assistance. Alternatively, the IVR system 612 may prompt the patient 620 to call a health care professional at the patient's convenience. The method which the remote processing system 604 selects may be based on the severity of the patient's health status as determined by the one or more scores. Thus, for example, if the one or more scores indicate the patient is within a few points of an adequate score, the remote processing system 604 may select a greater time period during which it initiates communication with the patient. However, if one or more of the patient's scores are significantly outside of the range of an acceptable score as determined by the threshold values, the remote processing system 604 may determine that immediate medical assistance is required without further communication with the patient 620.

If the central processing unit 614 determines that the patient 620 is in need of a follow-up consultation with the IVR system 612 within a certain time period after the present call, the central processing unit 614 may add the patient 620 to a prepared queue of callers that the IVR system 612 has been programmed to call automatically. Such a queue may be updated by a health care professional and/or the central processing unit 614. As such, the IVR system 612 will automatically initiate interaction with the patient 620 at a predetermined time in the future based on the patient's position in the queue. More information relating to the decision-making of the central processing unit 614 in response to patient answers is described in greater detail in the co-pending patent application entitled, DOWNLOADABLE DATASETS FOR A PATIENT MONITORING SYSTEM, which was previously incorporated by reference herein in its entirety.

Figure 11:
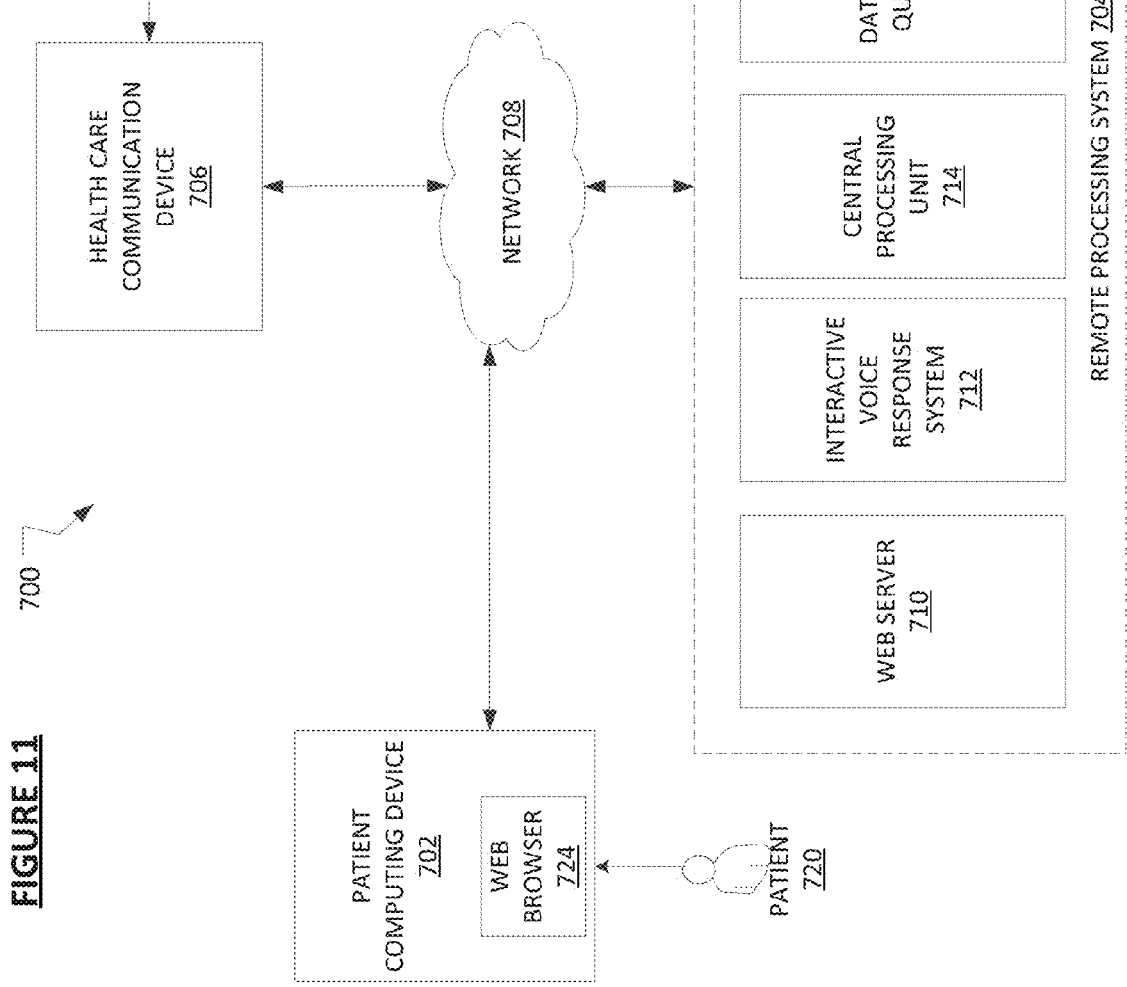
FIG. 11 is a schematic diagram illustrating another embodiment of a patient monitoring system including a patient computing device utilizing a web browser.

FIG. 11 is a schematic diagram illustrating another example of a patient health monitoring system 700. The patient health monitoring system 700 includes a patient computing device 702, remote processing system 704, a health care communication device 706, and a network 708. The remote processing system 704 includes a web server 710, an interactive voice response ("IVR") system 712, a central processing unit 714, a database of questions 716, and a database of results 718. The patient computing device 702 can be operated by a patient 720 by either directly or indirectly accessing a web browser 724. The health care communication device 706 can be accessed and operated by a health care professional 722.

The system 700 is one example of the system 10 (FIG. 1), the computing device 702 is one example of the communication device 12, and the remote processing system 704 is one example of the remote processing system 18. It is understood that, though not shown, the system 700 may include one or more monitoring apparatuses as discussed above, such as, for example, the monitoring apparatuses 14.

In use, the patient health monitoring system 700 operates similarly to the patient health monitoring system 600. However, in the current embodiment, the patient interacts with the remote processing system 704 by way of the patient computing device 702. The patient computing device 702 connects to the web server 710 through the network 708.

The patient computing device 702 may be located in the home of the ambulatory patient 720, or in some other location that is easily accessible to the patient 720. Examples of the patient computing device 702 may include a cellular telephone, a tablet, a computer, or other wireless or wired communication devices having access to a web browser. The patient 720 can utilize the computing device 702 to open the web browser 724 to initiate a communication session with the web server 710. In some embodiments, the web server 710 may communicate with the IVR system 712 (which functions similarly to the IVR system 612 discussed above). Alternatively, a family member of the patient 720 or other person in close proximity to the patient 720 and authorized by the patient 720 may utilize the computing device 702 on behalf of the patient 720 to initiate a communication session through the network 708 with the web server 710.

The patient 720 may directly or indirectly use the patient computing device 702 to access the web browser 724. For example, in one embodiment, the patient 720 may directly access a web browser 724 and type a URL into the web browser to access the remote processing system 704. In an alternate embodiment, the patient 720 is provided with purpose-built software for execution on the patient computing device 702 whenever the patient 720 wishes to interact with the remote processing system 704. This software may appear to be a purpose-built remote interface application to the patient 720. However, when executed, the software may do no more than initiate a web browser session to web server 710. In an embodiment, the software may be designed to limit the functionality of the web browser 724 to only interacting with the web server 710. As such, the software may display the web browser 724 on the patient computing device 702 in such a way that the patient 720 does not know he is viewing a web page from the remote processing system 704 on the web browser 724. Rather, through the software, the patient 720 may have the experience of interacting with a local application when, in fact, the patient 720 is interacting with the remote processing system 704. In some embodiments, the patient 720 may execute the software by selecting an icon on the display of the patient computing device 702. The patient 720 may select the icon by utilizing a mouse, stylus, or other like device. If the patient computing device 702 is a touch screen device, the patient 720 may utilize a finger to select the icon.

In other embodiments, the patient 720 may directly open the web browser 724 and input a web address into the web browser 724 to initiate communication with the web server 710 over the network 708.

Regardless of whether the patient is directly or indirectly accessing the web browser, after the web server 710 receives the initial page request, an initial page is generated by the central processing unit 714. The page is transmitted to the web server 710 which then sends the data over the network 708 to the patient computing device 702 which displays the page to the patient via the web browser 724. At this time, the patient 720 may begin interaction with the web server, via the web page, through the web browser 724. In one embodiment, the initial page may prompt the patient 720 with a first question of a question hierarchy. The question may be written in text format on the web browser display. In this embodiment, the question may be presented as a multiple choice question or as an open-ended question. Alternatively, the web server 710 may communicate with the IVR system 712 and present the question to the patient 720 in an audible format. Again, the question may be presented as a multiple choice question or as an open-ended question. In yet another embodiment, the question may be presented to the patient 720 in both a text and an audible format. In other embodiments, the initial page may prompt the patient 720 to provide the system with an identification code as discussed above in reference to FIG. 10.

In some embodiments, the patient 720 may respond to the first question by either selecting an answer which corresponds to the patient's answer or by typing an answer into a text box. Alternatively, the patient 720 may utilize an input device (not shown) such as a microphone, on the patient computing device 720 to verbally respond to the question. At this time, the answer data is sent over the network 708 to the web server 710. If the answer is not verbal, the data is processed at the central processing unit 714 which then selects the content of the next page to be displayed to the patient 720. Alternatively, if the answer is verbal, the IVR system 712 may first decode the response and then send this data to the central processing unit 714. The central processing unit 714 generates a second page, based on the database of questions 716 and the database of results 718, which is then sent to the patient computing device 702 by the web server 710 through the network 708. Details on how the central processing unit 714 determines which questions to present to the patient 720 is described in greater detail above in reference to FIG. 10.

The web pages presented to the patient 720 may vary based on the patient, the symptoms experienced by the patient, the responses presented to the system by the patient, and other like factors. For example, the web server 710 may transmit pages including one or multiple questions, feedback comments relating to health care related issues, teaching tips related to health care issues, or greeting and ending comments. The data on the pages may be only presented to the patient in a text format. However, in other embodiments, the data on the pages may be presented to the patient in an audible format, or both in a text and an audible format.

Based on the responses inputted by the patient 720, the central processing unit 714 calculates one or more scores as discussed above and may determine the patient is in need of professional medical assistance. In other embodiments, the central processing unit 714 may update scores that were originally calculated based on previous patient inputs, such as inputs from other devices such as cellular enabled devices, inputs from the IVR system described in FIG. 10 or other previous health data related to the patient 720 that is stored in the central processing unit 714. In response, the central processing unit 714 may generate a page indicating to the patient 720 that he should seek medical attention which is transmitted to the patient 720 via the web server 710 and loaded on the patient computing device 702. Alternatively, the central processing unit 714 may automatically contact the health care professional 722. In yet another embodiment, the central processing unit 714 may add the patient 720 to a prepared queue of callers that the IVR system 712 has been programmed to call automatically, as discussed in greater detail above in reference to FIG. 10.

In another embodiment, the central processing unit 714 may determine that the patient 720 is in need of a follow-up consultation. In response, the central processing unit 714 may generate a page indicating to the patient 720 that he should log-in to the application via the web browser 724 within a certain amount of time. Alternatively, the central processing unit 714 may automatically contact the health care professional 722 or a family member of the patient 720 or other third party that can remind the patient 720 to engage in the follow-up consultation at the later time determined by the central processing unit 714. This communication may occur through a phone call, text message, email, or the like. Further information relating to how the central processing unit 714 engages in decision-making is discussed above with reference to FIG. 10.

Figure 12:
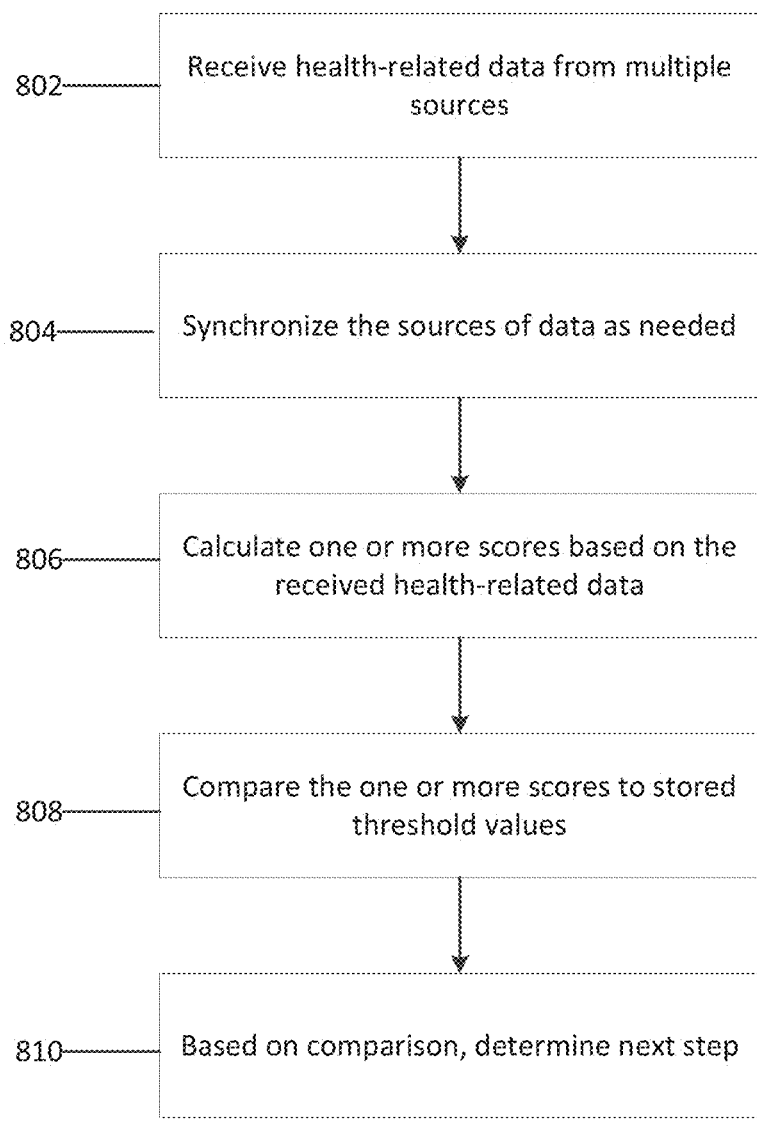
FIG. 12 is a flow diagram representing an embodiment of a method for receiving and processing patient data.

FIG. 12 is a flow diagram representing an embodiment of a method 800 for receiving and processing health-related data. According to some embodiments, some or all of the method 800 may be implemented at a remote processing system, such as the remote processing system 10. For purposes of clarity, the method 800 will be described with reference to the components described in the above discussed figures, however, it is understood that such description shall not be construed to be limiting.

The method 800 begins at operation 802 when health related data is received at the remote processing system 10 by multiple sources of data. Multiple sources of data include any of the monitoring apparatuses described herein (e.g., monitoring apparatuses 14), a patient communication device (e.g., communication device 602), and/or a patient computing device (e.g., computing device 702). The data may all be received simultaneously or at different intervals of time. The data may include patient answers to health-related questions, patient measurements (e.g., blood glucose, blood pressure, weight, blood oxygen level, temperature, biometrics, etc.), and/or the like.

The method 800 proceeds to operation 804. At operation 804, the remote processing system 10 synchronizes the sources of data as needed. For example, if patient answers from a first question hierarchy are received at operation 802 from one of the monitoring apparatuses 14, the remote processing system 10 determines that the first question hierarchy has been presented to the patient, and thus, no other monitoring device, communication device, and/or computing device needs to present the first question hierarchy to the patient. In such an example, the remote processing system 10 may transmit datasets to the remaining monitoring apparatuses, that when executed, cause the remaining monitoring apparatuses to not present the first question hierarchy to the patient for a certain amount of time, such as, for example, a day. This time period may vary based on the patient and the particular patient's health status.

Next, the method 800 proceeds to operation 806. At operation 806, one or more scores are calculated based on the received health-related data. Scores may be calculated based on condition, symptom, or overall health status. In general, a score for a particular piece of data represents the importance of that data in determining the particular condition, symptom, or overall health status of the patient in addition to a value indicative of the particular patient's answer and/or measurement.

For example, each piece of incoming data may be related to a certain condition or symptom. The data may be categorized based on related condition or symptom. In some examples, data may come from different sources of data but categorized together because they are related to the same condition or symptom. Each piece of data in the group may be assigned a particular value based on predetermined values stored at the remote processing system. The assigned value may indicate the importance of the particular data with respect to the particular condition or symptom, the patient's response or measurement, or both. In some embodiments, the values are added together within a group to determine an overall health score for the particular category. In some embodiments, an overall health score is determined which may include all received data.

At operation 808, the remote processing system 10 compares the calculated score(s) to one or more stored threshold values. As stated above, predetermined threshold values may be customized for the patient or generic to all patients and may be stored in a database at the remote processing system 10. In some embodiments, the predetermined threshold values are stored in a look-up table. The remote processing system 10 may access the look-up table and determine a threshold score for the particular condition, symptom, or overall health status.

Next, the method 800 proceeds to operation 810. At operation 810, the remote processing system 10 determines a next action. Based on operation 808, the system may determine if the patient's one or more scores are outside an acceptable range by comparing the one or more scores to the predetermined threshold values. The threshold values may be, for example, maximum or minimum score values. If the patient is within acceptable values, the remote processing system 10 may do nothing or determine that further data need not be collected for a certain amount of time. This may be a standard amount of time, such as, for example, 24 hours. However, if the scores indicate that patient data falls outside of acceptable healthy ranges, the remote processing system 10 may initiate further data collection immediately or within a shorter amount of time determined by the system. For example, the system may determine that further data to clarify the extent of the patient's health irregularities must be collected within the next two hours. The remote processing system 10 may have an internal timer which may be set at this time to ensure that further data is collected within the selected time period. To collect the data, the remote processing system 10 may awaken one or more of the remote monitoring apparatuses 14 and direct the monitoring apparatuses 14 to initiate communication sessions with the patient. The remote processing system 10 may also utilize an internal IVR system, as described above, to initiate an IVR system with the patient via a patient's communication or computing device.

In some examples, the patient may not interact with the monitoring apparatuses or pick up calls from the IVR system during the determined time period. In some embodiments, the remote processing system 10 may directly contact a health care professional in such cases. Alternatively, the remote processing system 10 may reset the timer for a shorter amount of time thereby providing the patient will supplemental time to interact with the system 10.

In some embodiments of the method 800, the raw data received at the remote processing system 10 is compared to previously stored data. Thus, in some embodiments, the system may not score every piece of incoming data, but instead compare the data with previously stored patient data. For example, if a weight measurement is received at the remote processing system 10, the remote processing system 10 may compare the weight measurement with a previous measurement, such as the last measurement taken or a symptom-free dry weight measurement. The difference of the weight measurement and the previously stored measurement may be compared with a threshold value, such as, for example, 0.5 lbs. If the difference is below the threshold value, the system 10 may determine that the importance of further data is low. However, if the difference is above the threshold value, the system 10 may determine that the importance of further data is high. In some instances, the comparison may be time dependent. That is, a larger difference between two measurements taken within a few hours of each other may indicate a greater need for further health-related data, whereas, the same difference between two measurements taken several weeks between each other may not indicate the same great need for further data.

Based on the need for further data, the system may determine a reminder time. A high need for further information may mean that the reminder time is lower, such as, for example, between the range of immediately to one week. One example of a lower reminder time is 15 minutes-120 minutes. A lower need for further information may mean that the reminder time is higher, such as, for example, one minute to one week. One example of a higher reminder time is one day to three days. An internal clock at the remote processing system 10 may track the reminder time. Once elapsed, the system may determine whether further information has been received at the remote processing system 10. If not, one or more of the monitoring apparatuses may initiate a communication session with the patient or present a reminder message on the display indicating to the patient that it is time to interact with the system. The reminder message may include audible noises, spoken messages, displayed text, displayed images, or the like. Alternatively or additionally, the system 10 may initiate a call via the IVR system to the patient communication device.

In yet further embodiments, the raw data received at the remote processing system 10 may be compared to a threshold value in addition to calculation of one or more scores which are also compared to threshold values. Based on each of the comparisons, the need for further information is determined and a reminder time may be set.

After operation 810, in some examples, the patient may interact with the monitoring apparatuses or the IVR system which causes the system to receive more health-related data.

The method 800 utilizes this data to again synchronize the devices as needed and update the calculated scores based on the newly provided information. Thus, it is understood that the method 800 may be continuous and is performed each time data is received at the remote processing system 10.

Below are non-limiting example embodiments of the method 800 in use.

EXAMPLE 1

A patient weighs on a wireless weigh scale at 7:30 AM. The patient's weight is 150.3 lbs. This weight data is transmitted to the central system. This weight is below the patient's maximum threshold of 155 lbs, and the patient's weight gain of 0.1 lbs in three days is below the patient's threshold of 0.3 lbs. The System scores this data and determines that the importance of further data is low. The system sets the reminder time for health information queries to the low level of 24 hours. Once the time elapsed from the last queries session is greater than the reminder time a call from the IVR system is placed to the user to start a query session so that further information can be gathered from the patient.

EXAMPLE 2

A user weighs on a wireless weigh scale at 7:30 AM. The user's weight is 155.3 lbs. This data is transmitted to the central system. This weight is above the user's maximum threshold of 155 lbs, and the user's weight gain of 0.1 lbs in 3 days is below the user's threshold of 0.3 lbs. The system scores this data and determines that the importance of further data is medium. The system sets the reminder time for health information queries to the medium level of two hours. Once the time elapsed from the last data transmission is greater than the reminder time, the in-home query device (e.g., monitoring device 14) wakes up and says "It is time to take your health check" to solicit a response from the user.

EXAMPLE 3

A user weighs on a wireless weigh scale at 7:30 AM. The user's weight is 153.3 lbs. This data is transmitted to the central system. This weight is below the user's maximum threshold of 155 lbs, and the user's weight gain of 0.4 lbs in five days is above the user's threshold of 0.3 lbs. The System scores this data and determines that the importance of further data is medium. The system sets the reminder time for health information queries to the medium level of two hours. At 7:45 AM the same user takes a blood pressure reading using a patient monitoring device. The reading is 160/102 mmHg. This data is transmitted to the central system. This blood pressure reading is above the user's maximum threshold of 150/90 mmHg. The system scores the weight and blood pressure data and determines that the importance of further data is high. The system sets the reminder time for health information queries to the high level of 15 minutes. Once the time elapsed from the last data transmission is greater than the reminder time, the in-home query device wakes up and says "It is time to take your health check" to solicit a response from the user.

EXAMPLE 4

A user weighs on a wireless weigh scale at 7:30 AM. The user's profile has been set to increase compliance. The system sets the reminder time for health information queries to the compliance level of 15 minutes. Once the time elapsed from the last data transmission is greater than the reminder time, a call from the IVR system is placed to the user to start a query session. This time is set on the basis of increasing the probability of soliciting a session before the user forgets or ignores the task.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present disclosure. Numerous other changes may be made which will readily suggest themselves to those skilled in the art and which are encompassed in the spirit of the disclosure and as defined in the appended claims.

What is claimed is:

1. A patient monitoring system, comprising:
    a first monitoring device arranged and configured to collect data related to a first health parameter of a patient;
    a second monitoring device arranged and configured to collect data related to a second health parameter of a patient;
    a remote processing system coupled to the first and second monitoring devices via a network, the remote processing system arranged and configured to:
        receive the data related to the first health parameter and a first data collection time from the first monitoring device;
        independently receive the data related to the second health parameter and a second data collection time from the second monitoring device;
        calculate a score based on at least one of the first and second health parameters;
        compare the score to a threshold value; based on the comparison, determine a reminder time; and
        when the reminder time has elapsed, trigger at least one of the first and second monitoring devices to remind the patient to interact with the system via a reminder message;
        select a question hierarchy based upon the health parameter used to calculate the score;
        present at least one question from the question hierarchy to the patient using the first monitoring device;
        receive at least one answer to the at least one question from the patient; and
        synchronize the second monitoring device with the first monitoring device by presenting, to the patient via the second monitoring device, additional questions from the question hierarchy based upon the at least one answer having been received.

2. The patient monitoring system of claim 1, wherein the remote processing system is further configured to establish a communication session with a computer that is configured to collect data related to the first health parameter of the patient via a web-browser, wherein the collected data includes answers to questions presented to the patient via the web-browser.

3. The patient monitoring system of claim 1, wherein the reminder message includes at least one of: audible noises, spoken messages, and a displayed text.

4. The patient monitoring system of claim 1, wherein the reminder message is a call from the remote processing system via an interactive voice response system.

5. The patient monitoring system of claim 1, further comprising:
    at least one third monitoring device collecting health parameter data of a patient; the at least one third monitoring device coupled to the remote processing system via the network.

6. The patient monitoring system of claim 1, wherein the remote processing system is further arranged and configured to:
    calculate a first individual score related to the first health parameter; calculate a second individual score related to the second health parameter;
    compare the first individual score to a first threshold value; compare the second individual score to a second threshold value;
    based on comparing the first individual score to the first threshold value, determine a first time period during which further information must be collected related to the first health parameter; and
    based on comparing the second individual score to the second threshold value, determine a second time period during which further information must be collected related to the second health parameter.

7. The patient monitoring system of claim 6, wherein the first threshold value and the second threshold value are previous patient measurements.

8. The patient monitoring system of claim 7, wherein at least one of the first and second threshold values are answers to health-related questions.

9. The patient monitoring system of claim 1, wherein the threshold value is a maximum score value.

10. The patient monitoring system of claim 1, further comprising:
    a patient communication device arranged and configured to connect to the remote processing system via the network;
    wherein the remote processing system is further arranged and configured to:
    automatically initiate a communication session with the patient through the interactive voice recognition system;
    receive the responses from the patient;
    update the first score based on the responses from the patient; and
    update the reminder time based on the updated first score.

11. The patient monitoring system of claim 1, further comprising:
    a patient computing device pre-programmed with software, wherein executing the software causes the patient computing device to:
    access a third-party application stored on the patient computing device;
    automatically initiate communication between the third-party application and the remote processing system;
    receive a webpage including a plurality of questions from the remote processing system;

present the webpage including the plurality of health-related questions to the patient, wherein the webpage is customized with an appearance of webpages generated by the third-party application; and send patient responses to the health-related questions to the remote processing system.

12. The patient monitoring system of claim 11, wherein the software is executed upon patient selection of an icon on a display of the patient computing device.

13. The patient monitoring system of claim 11, wherein the score is updated based on the responses.

14. The patient monitoring system of claim 1, wherein the remote processing system is further arranged and configured to notify a health care professional about the patient's health status if the patient does not respond to the reminder message within a predetermined amount of time.

15. The patient monitoring system of claim 1, wherein the remote processing system is further arranged and configured to determine, based on the comparison, an importance level of further information from the patient.

16. The patient monitoring system of claim 1, wherein the remote processing system is further configured to:

determine a first amount of time by comparing the health score to one or more threshold values;

initiate, based upon the first amount of time, an internal timer;

awaken, in response to the internal timer, at least one of the monitoring devices;

provide, using the awakened at least one monitoring devices, an alert requesting interaction by the patient;

reset the internal timer to a second amount of time; and alert, in response to a lack of patient interaction during the second amount of time, a health care processional.

17. The patient monitoring system of claim 1, wherein the remote processing system is further configured to:

establish communication to a telephone associated with the patient; and synchronize, based upon the at least one answer having been received, the telephone by presenting, using the telephone, additional questions from the question hierarchy to the patient.

* * * * *